(12) United States Patent
Saar et al.

(10) Patent No.: US 11,207,256 B2
(45) Date of Patent: Dec. 28, 2021

(54) METHOD FOR SOLUBILIZING POORLY WATER-SOLUBLE COSMETIC AGENTS

(71) Applicant: ATHENION AG, Zug (CH)

(72) Inventors: Ingo Saar, Niederkassel (DE); Wolfgang Brysch, Berlin (DE); Jörg von Wegerer, Berlin (DE)

(73) Assignee: ATHENION AG, Zug (CH)

( * ) Notice: Subject to any disclaimer, the term of this patent is extended or adjusted under 35 U.S.C. 154(b) by 0 days.

(21) Appl. No.: 16/624,167

(22) PCT Filed: Jun. 28, 2018

(86) PCT No.: PCT/EP2018/000326
§ 371 (c)(1),
(2) Date: Dec. 18, 2019

(87) PCT Pub. No.: WO2019/001770
PCT Pub. Date: Jan. 3, 2019

(65) Prior Publication Data
US 2020/0170915 A1    Jun. 4, 2020

(30) Foreign Application Priority Data
Jun. 30, 2017 (EP) .................... 17001119

(51) Int. Cl.
*A61K 8/55* (2006.01)
*A61K 8/11* (2006.01)
(Continued)

(52) U.S. Cl.
CPC ............... *A61K 8/553* (2013.01); *A61K 8/11* (2013.01); *A61K 8/14* (2013.01); *A61K 8/345* (2013.01);
(Continued)

(58) Field of Classification Search
CPC ........ A61K 49/0052; A61K 8/11; A61K 8/14; A61K 8/31; A61K 8/34; A61K 8/345; A61K 8/37; A61K 8/64; A61K 8/9789; A61K 8/9794; A61K 9/00; A61K 9/0031; A61K 9/0051; A61K 9/006; A61K 9/007; A61K 9/0085; A61K 9/0092; A61K 9/06; A61K 9/10; A61K 9/107; A61K 9/1275; A61K 9/141; A61K 9/146; A61K 9/16; A61K 9/2086; A61K 9/4825; A61K 9/50; A61K 9/5031; A61K 9/51; A61K 9/5115; A61K 9/5153; A61K 9/5161; A61K 9/5192; A61K 9/70; A61K 9/7038; A61K 2300/00; A61K 38/177; A61K 38/1774; A61K 9/0019; A61K 45/06; A61K 31/713; A61K 31/20; A61K 9/1272; A61K 31/7088; A61K 9/5123; A61K 31/7105; A61K 35/18; A61K 39/001; A61K 39/385; A61K 47/6901; A61K 9/5068; A61K 31/685; A61K 47/10; A61K 9/1271; A61K 31/202; A61K 47/14; A61K 31/337; A61K 31/352; A61K 31/568; A61K 31/573; A61K 9/0053; A61K 9/127; A61K 2800/10; A61K 31/4402; A61K 31/496; A61K 31/675; A61K 31/7068; A61K 38/00; A61K 47/24; A61K 47/26; A61K 47/32; A61K 9/145; A61K 9/1617; A61K 9/4858; A61K 31/201; A61K 31/355; A61K 31/505; A61K 31/704; A61K 47/12; A61K 47/22; A61K 47/28; A61K 47/44; A61K 47/543; A61K 48/0033; A61K 9/0014; A61K 9/0043; A61K 9/08; A61K 9/14; A61K 9/1676; A61K 9/19; A61K 31/18; A61K 31/34; A61K 31/343; A61K 31/4375; A61K 31/519; A61K 31/52; A61K 31/522; A61K 31/5377; A61K 31/555; A61K 31/57; A61K 31/58; A61K 31/683; A61K 35/28; A61K 38/1709; A61K 38/2066; A61K 39/3955; A61K 47/18; A61K 47/20; A61K 47/60; A61K 47/6911; A61K 48/00; A61K 48/0025; A61K 8/361; A61K 8/375; A61K 8/553; A61K 8/678; A61K 8/922; A61K 9/0036; A61K 9/1277; A61K 9/1652; A61K 9/48; A61K 9/5015; A61K 9/5084; A61K 9/5146; A61K 9/7023; A61K 2035/122; A61K 2035/124; A61K 2039/505; A61K 31/05; A61K 31/4709;
(Continued)

(56) References Cited

U.S. PATENT DOCUMENTS

| 8,518,378 B2 | 8/2013 | Tamarkin et al. |
| 2004/0192768 A1 | 9/2004 | Behnam |
| 2012/0277195 A1 | 11/2012 | Banov et al. |

FOREIGN PATENT DOCUMENTS

| DE | 198 57 492 A1 | 6/2000 | |
| DE | 19857492 | * 6/2000 | ............... A61K 8/19 |

(Continued)

OTHER PUBLICATIONS

DE19857492A1 translation (Year: 2000).*
(Continued)

Primary Examiner — Audrea B Coniglio
(74) Attorney, Agent, or Firm — Haug Partners LLP

(57) ABSTRACT

The present invention relates to a method for solubilizing poorly water-soluble organic cosmetic agents, to the solubilisate and cosmetic preparations produced by this method and respective uses of the solubilisate in cosmetic preparations. A phosphatidylcholine-based solubilization method is disclosed.

13 Claims, No Drawings

(51) Int. Cl.
*A61K 8/14* (2006.01)
*A61K 8/34* (2006.01)
*A61K 8/36* (2006.01)
*A61K 8/67* (2006.01)
*A61Q 11/00* (2006.01)
*A61Q 17/04* (2006.01)
*A61Q 19/00* (2006.01)

(52) U.S. Cl.
CPC .............. *A61K 8/361* (2013.01); *A61K 8/678* (2013.01); *A61Q 11/00* (2013.01); *A61Q 17/04* (2013.01); *A61Q 19/00* (2013.01); *A61K 2800/522* (2013.01); *A61K 2800/805* (2013.01)

(58) Field of Classification Search
CPC ............ A61K 31/5383; A61K 31/5513; A61K 31/7048; A61K 35/612; A61K 35/74; A61K 47/02; A61K 47/183; A61K 47/186; A61K 47/36; A61K 47/38; A61K 47/549; A61K 8/06; A61K 8/062; A61K 8/342; A61K 8/36; A61K 8/63; A61K 8/927; A61K 9/0024; A61K 9/0048; A61K 9/0073; A61K 9/1623; A61K 9/1635; A61K 9/1641; A61K 9/20; A61K 9/2013; A61K 9/2018; A61K 9/2031; A61K 9/2054; A61K 9/2059; A61K 9/4841; A61K 9/4866; A61K 9/5026; A61K 9/5078; A61K 2039/545; A61K 2236/00; A61K 2800/30; A61K 2800/34; A61K 2800/522; A61K 2800/805; A61K 31/00; A61K 31/145; A61K 31/155; A61K 31/192; A61K 31/197; A61K 31/353; A61K 31/395; A61K 31/397; A61K 31/40; A61K 31/4168; A61K 31/4427; A61K 31/4433; A61K 31/4439; A61K 31/444; A61K 31/4725; A61K 31/53; A61K 31/688; A61K 31/711; A61K 31/712; A61K 31/7125; A61K 31/728; A61K 31/80; A61K 33/00; A61K 35/17; A61K 35/57; A61K 35/618; A61K 36/185; A61K 38/1816; A61K 39/39541; A61K 47/40; A61K 47/42; A61K 47/542; A61K 47/544; A61K 47/545; A61K 47/62; A61K 47/64; A61K 47/6849; A61K 47/6909; A61K 47/6913; A61K 47/6917; A61K 47/6923; A61K 47/6929; A61K 47/6935; A61K 48/0008; A61K 48/005; A61K 48/0083; A61K 49/00; A61K 49/0008; A61K 31/7052; A61K 36/82; A61K 31/122; A61K 31/549; A61K 9/0095; A61K 9/1075; A61K 31/015; A61K 31/341; A61K 31/443; A61K 31/4525; A61K 31/4965; A61K 36/258; A61K 36/324; A61K 36/9068; A61K 47/34; A61K 47/6951; A61P 43/00; A61P 35/00; A61P 37/02; A61P 37/06; A61P 25/00; A61P 1/04; A61P 3/10; A61P 13/12; A61P 17/00; A61P 7/06; A61P 9/00; A61P 1/00; A61P 1/16; A61P 29/00; A61P 7/00; A61P 31/12; A61P 37/00; A61P 25/28; A61P 3/06; A61P 7/02; A61P 9/10; A61P 19/02; A61P 19/10; A61P 21/02; A61P 25/06; A61P 25/16; A61P 31/04; A61P 35/02; A61P 7/04; A61P 9/12; A61P 15/00; A61P 15/06; A61P 25/08; A61P 25/20; A61P 25/22; A61P 25/24; A61P 31/00; A61P 31/10; A61P 31/18; A61P 37/08; A61P 3/04; A61P 11/00; A61P 13/08; A61P 15/08; A61P 15/10; A61P 15/12; A61P 15/18; A61P 17/06; A61P 17/08; A61P 17/10; A61P 17/12; A61P 19/06; A61P 21/04; A61P 25/04; A61P 25/26; A61P 27/02; A61P 33/06; A61P 33/10; A61P 37/04; A61P 3/02; A61P 5/00; A61P 5/16; A61P 5/24; A61P 5/30; A61P 5/40; A61P 7/10; A61P 9/04; A61P 9/06; A61P 11/02; A61P 13/00; A61P 13/06; A61P 1/12; A61P 1/18; A61P 21/00; A61P 23/00; A61P 25/18; A61P 25/30; A61P 25/32; A61P 27/16; A61P 31/14; A61P 31/20; A61P 31/22; A61P 35/04; A61P 39/00; A61P 3/00; A61P 3/12; A61P 3/14; A61P 5/50; A61P 9/08

See application file for complete search history.

(56) References Cited

FOREIGN PATENT DOCUMENTS

| DE | 19857492 A1 * | 6/2000 | ............... A61K 7/40 |
| EP | 1 591 020 A1 | 11/2005 | |
| WO | WO 2012/109151 A1 | 8/2012 | |
| WO | WO2012/109152 * | 8/2012 | ............. A61K 31/74 |
| WO | WO2012/109152 A1 * | 8/2012 | ............. A61K 31/74 |
| WO | WO 2012/109152 A1 | 8/2012 | |

OTHER PUBLICATIONS

DE19857492 translation (Year: 2000).*
International Search Report and Written Opinion dated Oct. 1, 2018 in corresponding International Application No. PCT/EP2018/000326.

* cited by examiner

METHOD FOR SOLUBILIZING POORLY WATER-SOLUBLE COSMETIC AGENTS

CROSS-REFERENCE TO RELATED APPLICATIONS

This application is the National Stage entry under 35 U.S.C. § 371 of International Application No. PCT/EP2018/000326 filed on Jun. 28, 2018, published on Jan. 3, 2019 under Publication Number WO 2019/001770 A1, which claims the benefit of priority under 35 U.S.C. § 119 of European Patent Application Number EP17001119.1 filed on Jun. 30, 2017, the entireties of which are herein incorporated by reference.

The present invention relates to a method for solubilizing poorly water-soluble cosmetic agents, to the solubilisate and cosmetic preparations produced by this method, respective uses of the solubilisate in a cosmetic preparation.

The skin provides a highly effective barrier for the permeation of xenobiotics and loss of water. Cosmetic agents or solutions, respectively cosmetic bases containing cosmetic agents should be provided in a homogeneous form in order to ensure a high efficacy. However, compounds with a different polarity can be hardly combined in a stable formulation. This may be effected by using an emulsifier. They have the disadvantage of relatively high costs and of an increased irritation potential and in many cases of impaired sensory characteristics. Emulsifiers may even bias the release of cosmetic agents from the composition. Fluids can be hardly combined with solid particles, as they tend to separate because of different densities. This may be overcome by using certain gel formers or solubilizers. But they are also relatively costly and impair likewise the sensory feeling of the cosmetic product on the skin. Also the spreading properties on the skin are often insufficient.

Monophasic hydrophilic systems, e.g. aqueous solutions, are ideal for hydrophilic cosmetic agents but lipophilic components such as oils and perfumes can only be used when they are embedded e.g. in wax beads or upon being solubilized with a solubilizer. In emulsions the use of an emulsifier is needed to mix the hydrophilic and the lipophilic phase in a stable manner, however with the drawbacks mentioned before.

A broad variety of substances is known for which potentially beneficial cosmetic effects have been suggested. The use of many of them, however, has been seriously limited by the poor solubility that can be achieved in cosmetic preparations known in the state-of-the-art. This is often due to the lipophilic nature of the cosmetic agent and a mainly polar character of the cosmetic preparation. Therefore skin penetration and the desired cosmetic effects cannot be attained to a satisfactory degree by such cosmetic agents. Hence, the use of such substances as cosmetic agent is limited when using standard cosmetic preparations.

There is a variety of approaches for improving the solubility of such cosmetic agents by using solubilization techniques. Herein the solubility of a substance in a medium is augmented by adding a third substance. These third substances are referred to as solubilizers (solubilizing agents), substances that may for example build a complex with the cosmetic agent to be solubilized. Examples for such chelating agents are sodium benzoate and sodium salicylate.

Another mechanism of action of solubilizers is the augmentation of the dissolving capacity of the solvent, for example by disturbing the cluster structure of water. Examples for such structure breakers are glycerol (glycerin) and macrogols (polyethylene glycol, PEG).

A third solubilization mechanism are micelle and liposome application technologies. They have won broad attention throughout the last decades. Herein the cosmetic agent to be delivered is enclosed in a spherical aggregate of surfactant molecules. These molecules are characterized by a polar head group and a long nonpolar chain ("tail"). When given into an aqueous medium these molecules tend to associate by aggregating to spherical structures by orienting the polar head group towards the surrounding medium and the nonpolar chain towards the interior of the spheres. When these spheres consist of only one layer of such amphiphilic molecules they are referred to as micelles. Depending on the nature of the amphiphilic molecule and the reaction conditions it is also possible to form spheres with more than one layer. Herein a second layer is formed inside the outer layer of the sphere, the nonpolar groups of this second layer being oriented towards the nonpolar groups of the outer layer, and the polar head groups being oriented towards the interior of the sphere. Such aggregates are referred to as liposomes. In their structure they resemble the lipid bilayer of the cell membrane. There are also multi-layered liposomes in which at least two liposomal spheres are formed around one another, thus building a multispherical aggregate. When given in a lipophilic medium these substances tend to build inversed spherical structures where the lipophilic chain is oriented towards the solution medium and the other layers are arranged accordingly.

Different uses of such loaded spheres have been described in the art, among them the usage as a topical application form for lipophilic substances in cosmetics and/or for increasing the skin penetration of the enclosed cosmetic agent. In micelles, the enclosed nonpolar substance concentrates in the interior space of the sphere toward which the nonpolar chains of the amphiphilic molecules are oriented. In liposomes, however, the interior space of the spheres is an aqueous, respectively hydrophilic medium. It can serve for packaging hydrophilic molecules. Poorly water-soluble, respectively lipophilic molecules, however, gather mostly in between the lipophilic structures of the liposomal layers.

Micelle- and liposome-based solubilisates for solubilizing cosmetic agents are disclosed e.g. in US 2012/219600 or U.S. Pat. No. 7,794,694.

Liposome-containing cosmetic formulations are commonly used to counteract epidermal water loss. In particular, the stratum corneum as the outermost layer of the epidermis may dehydrate. In normally hydrated or over-hydrated skin this is, however, not desirable. Like in pharmaceutical formulations, liposomes can be used as cosmetic delivery systems. A variety of applications has been described so far. The most common application is an improved dermal delivery of hydrophilic or amphiphilic cosmetic agents. They are solved in the aqueous environment of the interior space of the liposomes. Liposomes as a delivery system for lipophilic, respectively poorly water-soluble cosmetic agents gathering in the lipid bilayer are less common. The aforementioned problem of a possibly undesired skin hydration is also present in liposomal delivery systems. A further problem is the low solubility of the liposomes themselves in water. Thus they often need to be formulated together with a solubilizer or an emulsifier such as polysorbate (Tween) 20 or 80. However, there is an ongoing controversy about a detrimental impact of polysorbates on health (see below). Liposomes have a relatively short half-life. In consequence, liposome-based cosmetics have a relatively short shelf life. This is a limiting factor for their commercialization.

The short halflife is often due to that some of the liposomal phospholipids undergo oxidation and hydrolyzation.

As a result, there is a leakage of the encapsulated substances. It isn't trivial to foretell how large this leakage will be, so the needed amount of an encapsulated cosmetic agent cannot be simply increased by a leakage factor. Particularly in the case of a leakage of such an encapsulated cosmetic agent there is the risk that the cosmetic agent enters the eyes or the nasolabial region where it could be absorbed systemically via the mucosae. For most cosmetic agents and because of regulatory reasons systemic effects are not desirable for cosmetic agents. The greatest disadvantage of liposomal formulations, however, are the relatively high production costs. While this may be secondary in a pharmaceutical formulation it is a crucial factor for cosmetic products in a competitive market.

Micelle-based formulations have mostly the same advantages and disadvantages as liposome-based formulations of cosmetic agents. A further disadvantage is a lower loading capacity and a lesser stability (higher leakage) in comparison to liposomes (cf. Nishiyama and Kataoka, Pharmacol Ther 2006, 112, 630-648).

Although systemic adverse side effects of liposomal formulations may be not a major problem in cosmetic products some caution must be exercised, as liposomes carry the risk of accumulating in the liver, the spleen and/or the bone marrow, when they become systemically available.

Another solubilization technique is the formation of inclusion complexes of the substance to be solubilized with cyclodextrins such as α-, β- or γ-cyclodextrin or cyclodextrin derivatives such as 2-hydroxypropyl-β-cyclodextrin, methyl-β-cyclodextrin or trimethyl-β-cyclodextrin. Typically, cyclodextrins are composed of 6 to 8 1,4-linked α-D-glucopyranosides forming macrocycles. Thus a water-soluble toroid (cone-shaped or bucket-shaped) structure is generated which is capable to host hydrophobic substances in its interior. The interior space is considerably less hydrophilic than the outside contacting the aqueous environment. Cyclodextrins are produced from starch by enzymatic treatment. They are loaded with the compound to be solubilized by dispersion. The compound to be solubilized can then be released by contacting these complexes with water, by pH or temperature changes, depending on the specific composition. One drawback from cyclodextrin-based formulations occurs if a cosmetic agent does not dissociate rapidly. The release kinetics of the poorly water-soluble cosmetic agent may be altered as release is not immediate. Nephrotoxicity problems have also been described, when it becomes systemically available. However, the development of cyclodextrin formulations is apparently not easy and relatively costly. This limited their use until now (cf, Buschmann and Schollmeyer, J Cosmet Sci 2002, 53, 185-191; Numanoğlu et al., AAPS PharmSciTech 2007, 8, E1-E9; EP 0867175A1; WO 97/20861).

Thus, all these techniques have their advantages but also some drawbacks.

Polysorbates are widely used in these solubilization techniques. However, there is an ongoing controversy about a detrimental impact of polysorbates on health. Polysorbate-20 is discussed to be contaminated with unreacted 1,4-dioxane and ethylene oxide (at least from some suppliers). These are known skin-permeable carcinogenic substances (cf. FDA 1999, 21 CFR Part 173, Federal Register Vol 64, No. 104, pp. 29224-29227). A further problem of polysorbates such as Tween 80 is that they reduce the efficacy of widely used preservatives such as parabens by binding them (cf. Blanchard et al., Effect of sorbitol on interaction of phenolic preservatives with polysorbate 80, 1977, J Pharm Sci 66, p. 1470-1473). The paraben concentration, however, should not be increased accordingly because of their estrogenic potential (cf. Okubo et al.; ER-dependent estrogenic activity of parabens assessed by proliferation of human breast cancer MCF-7 cells and expression of ER-alpha and PR; 2001, Food Chem Toxicol 39, p. 1225-1232). Other well-known problems of polysorbates (in particular polysorbate 80) are hypersensitivity reactions of patients (cf. Steele et al., Hypersensitivity reactions to the polysorbate contained in recombinant erythropoietin and darbepoietin, Nephrology, 2005, 10, p. 317-320; Norris et al., Polysorbate 80 hypersensitivity reactions: a renewed call to action, Commun Oncol, 2010, 7, 425-428). Another problem with the use of polysorbates is that they facilitate a premature spontaneous self-emulsification. In consequence, comparatively higher shear forces are needed for a proper solubilization.

It is therefore desirable to dispose of a method for solving lipophilic cosmetic agents in a hydrophilic solution for cosmetic purposes without the use of an emulsifier or a stabilizer. The efficacy of a cosmetic agent may be impaired when not being properly solubilized in the fluid. Skin lipids or sweat are usually not sufficient to act as a natural solubilizer.

In a further aspect of the invention it may be also desirable to attain an improved skin penetration by using a solubilisate according to the invention of a lipophilic cosmetic agent in a lipophilic cosmetic base, and thus to improve the homogeneity of the cosmetic product. The skin penetration of such a cosmetic agent could thus be clearly improved without using a penetration enhancer that may be sometimes problematic.

Therefore there is a need to provide an alternative method for solubilizing poorly water-soluble cosmetic agents. It should fulfil the following criteria:
   easy-to-handle
   no lengthy development time for finding a favorable composition
   no costly equipment needed
   inexpensive materials and production costs
   applicable for a broad range of poorly water-soluble cosmetic agents
   no addition of polysorbate (Tween) solubilizers needed As the obtainable price on the market price is often limited for cosmetic products the net production costs are ever the more a crucial issue.

Surprisingly, it was found that the method according to the invention is able to solve this task.

Herein, at least one cosmetic agent is solubilized by the method according to the invention, comprising the following steps:
   a) Providing at least one cosmetic agent in the overall range of 0.5% to 25% per weight at room temperature and a pressure of 0.2 bar to 1 bar;
   b) Adding in any sequence the solubilization agents of at least one phosphatidylcholine in the overall range of 20% to 80% per weight,
      at least one medium-chained triglyceride in the overall range of 10% to 70% per weight,
      at least one lysophosphatidylcholine in the overall range of 1% to 15% per weight,
      at least one $C_2$ to $C_4$ alcohol in the overall range of 1% to 20% per weight, and at least one of glyceryl stearate or a saturated or unsaturated $C_{14}$ to $C_{20}$ fatty acid in the range of 0.5% to 10% per weight, respectively, wherein the relative weight percentages of all ingredients add up to 100% and all solubilization agents are independently from one another cosmetically acceptable excipients;

c) Cautiously heating the resulting mixture by continuously increasing the temperature with a temperature increment of 0.5° C./min to 3° C./min over a period of 15 to 60 minutes;

d) Stopping the temperature increase in a temperature range of 30° C. to 125° C. as soon as a clear solution is reached; and e) Letting the resulting solubilisate cool down to room temperature.

In a preferred embodiment this solubilization method is applied to a poorly water-soluble organic cosmetic agent:

a) Providing at least one poorly water-soluble organic cosmetic agent in the overall range of 0.5% to 25% per weight at room temperature and a pressure of 0.2 bar to 1 bar;

b) Adding in any sequence the solubilization agents of at least one phosphatidylcholine in the overall range of 20% to 80% per weight, at least one medium-chained triglyceride in the overall range of 10% to 70% per weight, at least one lysophosphatidylcholine in the overall range of 1% to 15% per weight, at least one $C_2$ to $C_4$ alcohol in the overall range of 1% to 20% per weight, and at least one of glyceryl stearate or a saturated or unsaturated $C_{14}$ to $C_{20}$ fatty acid in the range of 0.5% to 10% per weight, respectively, wherein the relative weight percentages of all ingredients add up to 100% and all solubilization agents are independently from one another cosmetically acceptable excipients;

c) Cautiously heating the resulting mixture by continuously increasing the temperature with a temperature increment of 0.5° C./min to 3° C./min over a period of 15 to 60 minutes;

d) Stopping the temperature increase in a temperature range of 30° C. to 125° C. as soon as a clear solution is reached; and e) Letting the resulting solubilisate cool down to room temperature.

A common scale to classify the degree of (water-)solubility consists of the following groups, reciting the parts of solvent required for one part of solute:

i) very soluble: <1
ii) freely soluble: 1-10
iii) soluble: 10-30
iv) sparingly soluble: 30-100
v) slightly soluble: 100-1000
vi) very slightly soluble: 1000-10000
vii) insoluble: >10000

According to the scope of the present application the term "poorly water-soluble" refers to the classes iv), v), vi) and vii). In other terms, a poorly water-soluble cosmetic agent according to the invention is a cosmetic agent that needs 30 or more parts of water for completely solubilizing one part of the cosmetic agent in water.

Another aspect of the invention is that the method according to the invention does not need polysorbates as solubilizers and/or emulsifiers. Therefore cosmetic agents can be solubilized by the method according to the invention, comprising the following steps:

a) Providing at least one cosmetic agent in the overall range of 0.5% to 25% per weight at room temperature and a pressure of 0.2 bar to 1 bar;

b) Adding in any sequence the solubilization agents of at least one phosphatidylcholine in the overall range of 20% to 80% per weight, at least one medium-chained triglyceride in the overall range of 10% to 70% per weight, at least one lysophosphatidylcholine in the overall range of 1% to 15% per weight, at least one $C_2$ to $C_4$ alcohol in the overall range of 1% to 20% per weight, and at least one of glyceryl stearate or a saturated or unsaturated $C_{14}$ to $C_{20}$ fatty acid in the range of 0.5% to 10% per weight, respectively, wherein the relative weight percentages of all ingredients add up to 100% and all solubilization agents are independently from one another cosmetically acceptable excipients;

c) Cautiously heating the resulting mixture by continuously increasing the temperature with a temperature increment of 0.5° C./min to 3° C./min over a period of 15 to 60 minutes;

d) Stopping the temperature increase in a temperature range of 30° C. to 125° C. as soon as a clear solution is reached; and e) Letting the resulting solubilisate cool down to room temperature.

This method is characterized in that the resulting solubilisate is devoid of polysorbate.

In a preferred embodiment this method refers to a poorly water-soluble organic cosmetic agent and is characterized in that the resulting solubilisate is devoid of polysorbate.

Urea is a popular excipient for solubilizing cosmetic agents. It may also act as a penetration enhancer e.g, for keratinic tissues. For the methods of the invention its use is not recommended, as it does not become solubilized during the solubilization process. It rather favors the generation of a suspension. Thus, the present application refers also to all methods of the invention disclosed herein, further characterized in that no urea is used for solubilization.

Confusing and even contradictory definitions can be found in the art. In order to avoid any ambiguity a solubilisate according to the invention is defined as follows:

A solubilisate is the composition of the at least one cosmetic agent to be solubilized and the solubilizing agents as defined according to the invention. Further addition of a solvent or diluent shall not be covered by this term. The solubilisate according to the invention is produced first by the solubilization method according to the invention, then a specific cosmetic preparation is produced with said solubilisate, and finally said cosmetic preparation is packaged into a suitable container for the respective cosmetic product.

The solubilisate according to the invention is characterized by the substantially complete solubilization of the substance (i.e. the cosmetic agent), thus being a nearly perfect solution in which the molecules behave substantially as independent entities in a solution and undergo the distribution and thermodynamic rules of Brownian motion. Thus the solubilisate is a clear solution containing the respective cosmetic agent(s) in a high concentration. In general, the solubilisate itself is not meant for direct use as a cosmetic product. In most cases, a portioned solubilisate accounts to a volume of a few milliliters.

A solubilisate according to the invention is fluid at room temperature.

In the methods for solubilization of a cosmetic agent according to the invention no water is used. The addition of water would even impair the solubilization process since it leads to an emulsification. The solubilisates produced by a method according to the invention are, however, self-emulsifying. Thus, the present application refers also to all methods of the invention disclosed herein, further characterized in that no water is used for solubilization.

In the scope of this patent application the terms "solubilization aggregate" or "solubilization essence" shall be used synonymously to "solubilisate".

A solubilisate must be differentiated from a suspension (colloidal suspension). This term defines a heterogeneous mixture containing solid particles that sooner or later will undergo sedimentation. It is also different from an emulsion (a mixture of two liquids which usually are immiscible). For increasing the bioavailability or skin penetration of a substance the complete solubilization is highly preferably. Therefore solubilisates are preferred over suspensions or emulsions.

A solubilisate according to the invention must be also be differentiated from a concentrate. A concentrate is a compound, respectively a composition of compounds without a diluent, respectively a cosmetic base. Upon mixing a concentrate with a cosmetic base the concentrate distributes itself either homogeneously within the cosmetic base, or may form a suspension or emulsion with the cosmetic base. A concentrate does not need the interaction with solubilizing agents, as it is intrinsically solvable in the respective medium of the cosmetic base.

A solubilisate according to the invention must also be differentiated from a lyophilizate that has been reconstituted in any form of solvent. Freeze-drying is a dehydration technique for preserving perishable compounds, e.g. cosmetic agents. A formulation of the at least one compound is frozen and then the surrounding pressure is reduced so that the frozen water in the material is sublimed directly from the solid phase to the gas phase. When properly sealed, the resulting lyophilizate can be stored at room temperature. Thus the shelf life of a sensitive product can be significantly increased. The product can be reconstituted by dissolving the lyophilizate in a suitable solvent. Often a lyoprotectant or cryoprotectant is added. The present invention does not refer to the generation of a lyophilizate, neither as a solid nor in a reconstituted form.

The term solubilisate used according to the invention must be differentiated from the cosmetic product. The cosmetic product according to the invention is generated by mixing the solubilisate according to the invention with the cosmetic base (the carrier formulation) and all cosmetic excipients. The cosmetic base has a much larger volume than the solubilisate (minimum: 10:1). The cosmetic product is the product ready for use by the consumer. The definition for "cosmetic preparation" or "cosmetic composition" is the same as for "cosmetic product", thus these terms are interchangeable.

The term "cosmetic product" comprises, without being limiting, eye cream, face cream, shower gel, foam bath, eau de toilette, eau de cologne, perfume, scent, fragrance, body lotion, body cream, hand care cream, moisturizing cream, nail moisturizing cream, toilette soap, deodorant, makeup, fluid makeup, rouge, powder, nail varnish, nail varnish remover, nail hardener, light stabilizer, self-tanning agent, eyeshadow, lipstick, lip gloss, lip balm, mascara, eyeliner pencil, eyelid liner, cleansing lotion, cleaning water, toothpaste, shampoo, antidandruff agent, hair conditioner, hairspray, hairstyling agent, hair shiner, permanent wave solution, hair dye, hair bleaching agent, hair decoloration agent, hair straightening agent, soap, skin whitening agent, exfoliant, syndet and pedicure product.

A diluent in the scope of the present application is a diluting agent (dilutant, thinner). It is not part of the solubilisate according to the invention.

In the scope of the present application the term "solubilizing agent" refers to any chemical substance that is added to the cosmetic agent for solubilizing it so that the cosmetic agent can be solved thereupon in an aqueous solution. The term "solubilizer" shall be used synonymously.

In alternative terms in the scope of the present application, "first liquid" refers to the "solubilisate" and "second liquid" to the "cosmetic product", if applicable.

In the scope of the present application the terms "cosmetic agent" and "cosmetic product" shall comprise agents and products that are suitable for a cosmetic use in humans and/or animals.

The method according to the invention is particularly suitable for the solubilization of lipophilic cosmetic agents. The most commonly used measure of lipophilicity is Log $P_{oct/wat}$, indicating the partition coefficient of a molecule between an aqueous and a lipophilic phase, usually water and 1-octanol. Eligible to be solubilized by the method of the invention are lipophilic cosmetic agents with Log P values $\geq 0$, preferred $\geq 0.5$, more preferred $\geq 1$, still more preferred $\geq 1.5$ and most preferred $\geq 2$.

In a preferred embodiment of the method according to the invention the at least one cosmetic agent is provided in the overall range of 2% to 15% per weight of the solubilisate, in a more preferred embodiment in the overall range of 2% to 10% per weight of the solubilisate.

Phosphatidylcholines are a class of phospholipids linked to choline. They are a major component of cell membranes and are for example obtained from egg yolk or soybeans. In practice, it showed that the origin of phosphatidylcholines influences their biological and chemical effects considerably. According to the invention the at least one phosphatidylcholine (PC) added as a solubilization agent can be selected from the group comprising 1-palmitoyl-2-oleoyl-sn-glycero-3-phosphocholine (POPC), natural (non-hydrogenated) or hydrogenated soy bean PC, natural or hydrogenated egg PC, dipalmitoyl phosphatidylcholine (DPPC), dimyristoyl phosphatidylcholine (DMPC) or 1,2-dioleyl-SN-glycero-3-phosphocholine (DOPC), 1-oleoyl-palmitoyl phosphatidylcholine (OPPC), diasteroyl phosphatidylcholine (DSPC), monostearoylphosphatidylcholine (MSPC), diarachidoylphosphatidylcholine (DAPC), and mixtures thereof. Preferred phosphatidylcholines are non-hydrogenated soy bean PC, DMPC, POPC and DOPC. Particularly preferred is non-hydrogenated soy bean PC.

Lecithin is commonly used as a synonym for phosphatidylcholines. It is a mixture of phosphatidylcholine and other compounds.

According to the method of the invention phosphatidylcholines are used in the overall range of 20% to 80% per weight of the solubilisate, preferred 40% to 70% per weight of the solubilisate, more preferred 50% to 65% per weight of the solubilisate and most preferred 60% per weight of the solubilisate.

Medium-chained triglycerides (MCT) refer to triglycerides the fatty acids of which have an aliphatic tail of 6-12 carbon atoms. Fatty acids incorporated in MCT are called medium-chain fatty acids (MCFA). In triglycerides three fatty acid molecules are bound to a glycerol backbone. Per definition, in MCT at least two of these three fatty acids must be MCFAs. According to the invention MCFA added as a solubilization agent can be selected independently from one another from the group comprising caproic acid, enanthic acid, caprylic acid, pelargonic acid, capric acid, undecilyc acid, lauric acid, their unsaturated derivatives, and mixtures thereof. Preferred MCFA are caproic acid, caprylic acid, capric acid, and lauric acid.

It can be advantageous in some embodiments of the invention to use triglycerides containing 1 to 3 myristic acid and/or palmitic acid residues instead of MCFAs. Hence, these two fatty acids can be incorporated into the MCT according to the invention too.

MCT oils or MCT fats are oils or fats containing predominantly said MCT. These terms refer to a respective mixture of different MCT that may contain a variety of MCFA. According to the invention any reasonable mixing ratio shall be covered by these terms. MCT fats are often extracted from specific plant fats, while MCT oils do not occur naturally. MCT oils and MCT fats are broadly marketed as a healthy dietary supplement, respectively as a surrogate for long-chain fats in the nutrition.

According to the method of the invention MCT added as a solubilization agent are used in the overall range of 10% to 70% per weight of the solubilisate, preferred 20% to 40% per weight of the solubilisate, more preferred 25% to 35% per weight of the solubilisate and most preferred 30% per weight of the solubilisate.

Lysophosphatidylcholines (LPC, lysoPC, also: lysolecithins) are a class of derivatives of phosphatidylcholines, resulting of their partial hydrolysis in which one of the fatty acid groups is removed. In the organism this hydrolysis is effected by the enzyme phospholipase A2. According to the invention the at least one lysophosphatidylcholine can be selected independently from one another from the group comprising all hydrolyzed compounds of the phosphatidylcholines listed above, 1-lysophosphatidylcholines (2-acyl-sn-glycero-3-phosphocholines), 2-lysophosphatidylcholines, L-alpha-lysophosphatidylcholine, and mixtures thereof.

According to the method of the invention lysophosphatidylcholines added as solubilization agents are used in the overall range of 1% to 15% per weight of the solubilisate, preferred 3% to 8% per weight of the solubilisate, more preferred 5% to 7% per weight of the solubilisate and most preferred 6% per weight of the solubilisate.

In the scope of the present application said lysophosphatidylcholines are not a mere variant or substitute for phosphatidylcholines but fulfill an independent role. Surprisingly, it was found that two solubilizing agents of similar but not identical chemical constitution can significantly improve the solubilizing effect, if used in an uneven ratio. Control experiments without lysophosphatidylcholines in which their relative weight percentage was substituted by a correspondingly higher amount of phosphatidylcholines only led to products having a higher viscosity. They had an appearance of a greasy stodge and couldn't be properly molten during heating. Thus, the lysophosphatidylcholines act as a co-solubilizing agent in the scope of the methods of the invention. According to the invention the ratio phosphatidylcholine to lysophosphatidylcholine is from 80:1 to 1.33:1, preferred 40:1 to 3:1, more preferred 25:1 to 5:1 and most preferred 20:1 to 8:1.

According to the invention the at least one $C_2$ to $C_4$ alcohol (lower alcohol) can be selected from the group comprising ethanol, propanol, isopropanol, butane-1-ol, butane-2-ol, and isobutanol (2-methyl-1-propanol). Preferred is ethanol.

According to the method of the invention $C_2$ to $C_4$ alcohols added as solubilization agents are used in the overall range of 1% to 20% per weight of the solubilisate, preferred 2% to 10% per weight of the solubilisate, more preferred 3% to 8% per weight of the solubilisate and most preferred 5% per weight of the solubilisate.

For achieving a complete solubilization the weight percentage of said at least one $C_2$ to $C_4$ alcohol is a critical amount. On the one hand, the at least one $C_2$ to $C_4$ alcohol supports the solubilization process. On the other hand, an excess of the at least one $C_2$ to $C_4$ alcohol may lead to a phase separation. In such a case the poorly water-soluble organic cosmetic agent has the tendency to precipitate, as the mixture becomes too surface-active. In most cases, however, a suitable weight percentage of the at least one $C_2$ to $C_4$ alcohol is inside the preferred ranges indicated above. A person skilled in the art will quickly find out which weight percentage of the at least one $C_2$ to $C_4$ alcohol is tolerable for a specific composition.

Thus the present application refers also to all methods of the invention disclosed herein, further characterized in that a phase separation of the resulting solubilisate due to an excess amount of the at least one $C_2$ to $C_4$ alcohol is avoided.

Glycols are often used as solubilzers for aqueous solutions of cosmetic agents. In the methods according to the invention, however, glycols such as ethylene glycol (ethane-1,2-diol), α-propylene glycol (propane-1,2-diol), β-propylene glycol (propane-1-3-diol), 1,2-butylene glycol (butane-1,2-diol), 1,3-butylene glycol (butane-1,3-diol), 1,4-butylene glycol (butane-1,4-diol), and diethylene glycol proved to be not suitable to be used instead of the aforementioned $C_2$ to $C_4$ alcohol. Their use leads to a clouding, respectively an opacification ("striping") of the solubilisates according to the invention. Clouding is an indicator of incomplete solubilzation. Different phases develop due to Ostwald ripening, respectively coalescence. Therefore the use of glycols for producing solubilisates according to the invention is discouraged.

Thus the present application refers also to all methods of the invention disclosed herein, further characterized in that no glycol is used for solubilization.

Glyceryl stearate (glycerol monostearate, GMS) is an emulsifier. The flaky powder is also hygroscopic. GMS is used as thickening, emulsifying, anti-caking, anti-staling and preservative agent.

According to the invention the at least one saturated or unsaturated $C_{14}$ to $C_{20}$ fatty acid can be used instead of glyceryl stearate. It can be selected from the group comprising myristic acid (14:0), pentadecanoic acid (15:0), palmitic acid (16:0), heptadecanoic acid (17:0), stearic acid (18:0), nonadecanoic acid (19:0), arachidic acid (20:0), myristoleic acid (14:1,cis-$\Delta^9$), palmitoleic acid (16:1, cis-$\Delta^9$), sapienic acid (16:1, cis-$\Delta^6$), hexadecatrienoic acid (16:3, (n-3), oleic acid (18:1, cis-$\Delta^9$), elaidic acid (18:1, trans-$\Delta^9$), vaccenic acid (18:1, trans-$\Delta^{11}$), linoleic acid (18:2; cis,cis-$\Delta^9,\Delta^{12}$), linoleadic acid (18:2, trans,trans-$\Delta^9\Delta^{12}$), α-linolenic acid (18:3, cis,cis,cis-$\Delta^9,\Delta^{12},\Delta^{15}$), γ-linolenic acid (18:3, (ω-3)), calendic acid (8E,10E,12Z-octadecatrienoic acid), stearidonic acid (18:4 (n-3)), dihomo-γ-linolenic acid (20:3; (ω-6)), eicosadienoic acid (20:2, (n-6)), eicosatrienoic acid (20:3, (n-3)), eicosatetraenoic acid (20:4, (n-3)), arachidonic acid (20:4, cis,cis,cis-$\Delta^5,\Delta^8,\Delta^{11},\Delta^{14}$), eicosapentaenoic acid (20:5, cis,cis,cis,cis,cis-$\Delta^5,\Delta^8,\Delta^{11},\Delta^{14},\Delta^{17}$). Preferred are even-numbered $C_{14}$ to $C_{20}$ fatty acids. Particularly preferred is oleic acid.

According to the method of the invention glyceryl stearate and/or a saturated or unsaturated $C_{14}$ to $C_{20}$ fatty acid added as solubilization agents are used in the overall range of 0.5% to 10% per weight of the solubilisate, preferred 1% to 8% per weight of the solubilisate, more preferred 2% to 6% per weight of the solubilisate and most preferred 3% per weight of the solubilisate.

The method according to the invention is usually run at room temperature. However, in alternative embodiments it may be also possible to preheat either the at least one cosmetic agent or any of the solubilizing agents to be added in step b) of the inventive method, provided that the preheating temperature does not exceed 28° C.

The method according to the invention can be performed at a pressure of 0.2 bar to 1 bar. It is preferred, however, to run the method at 1 bar (atmospheric pressure). For certain applications it may be preferable to use a light vacuum. The technical equipment for applying, maintaining and controlling such a light vacuum is well known in the art.

According to the method of the invention the resulting mixture is cautiously heated in step c) by continuously increasing the temperature over a period of 15 to 60 minutes. In preferred embodiments, this period is 20 to 40 minutes, and most preferred 25 to 35 minutes.

The heat increment can vary between 0.5° C./min to 3° C./min, preferred 1° C./min to 2° C./min and most preferred 2° C./min.

According to step d) the temperature increase is stopped in a temperature range of 30° C. to 125° C. as soon as a clear solution is reached. This moment depends heavily on the selected cosmetic agent as well as on the selected solubilization agents and reaction conditions. This can be further varied by the steepness of the temperature increase ramp, i.e. the relative temperature change per time unit. Apparently, it is not possible to foretell this "solubilizing temperature" on the basis of the specific components that are going to be used. Each composition of these components displays specific characteristics which have to be found out experimentally. Thus, it becomes to the experimenter to find out the optimal combination of these parameters which, however, is a standard process optimization for a person skilled in the art.

Running such a temperature ramp with a defined heat increment is essential for the methods according to the invention. A rash heating to a final temperature may lead to a disintegration of thermosensitive organic cosmetic substances and/or other ingredients. It also happens often with a rash heating that the solubilisates are not properly molten during the process. There is an excess of melt energy. In consequence, such a solubilisate tends to become cloudy or opaque during the cooling down step or afterwards which is detrimental for the stability of the solubilisate.

On the other hand, a heating that is too slow leads tendentially to an evaporation of the alcohol from the solubilization mixture. A hydrolytic decomposition, respectively a thermal degradation of sensitive organic cosmetic agents may occur, at least partially. The peroxide value is a key number for the content of peroxidic groups of a fat or a fatty oil. It is an indicator for its rancidity. It may increase significantly when the heating step is extended unnecessarily long.

Therefore it is mandatory to find a good balance for the heat increment of the temperature ramp.

An essential feature of the method according to the invention is the temperature control (temperature increment per time and duration of the heating). While there is a variability in the relative amounts of the solubilizing agents the controlled temperature increase is essential. Surprisingly, it was found that there is an optimal window for each substance to be solubilized. The exact values are difficult to predict, they have to be found out empirically. It is assumed that there is also an interdependency with the selected solubilizing agents and their relative amounts.

It is understood that the method according to the invention can be varied in such a way that any of the solubilizing agents of step b) can be provided first and then the at least one cosmetic agent as well as the other solubilizing agents can be added in any sequence. This variation was found to be neutral to the outcome of the method according to the invention.

In a preferred embodiment said mixture of the solubilizing agents of step b) and said at least one cosmetic agent are provided in a two-compartment system. This may facilitate the solubilization process according to the invention and each compartment can be marketed separately. For certain cosmetic agents this can be advantageous for the stability and thus for the stability of the solubilisate or the cosmetic product according to the invention.

The moment when the resulting solubilisate has become a clear solution is determined by observation of the experimenter. In general, this moment is achieved when the solution appears transparent and does not display any sedimentation, precipitation, slurs, smears or striping (zebra effect).

In an alternative embodiment the parameters for the temperature ramp according to the invention that have been determined as described before can be implemented in an automatized or half-automatized device setting. This may be advantageous, for example, in an upscale industrial application.

The solubilisates produced according to the method of the invention maintain this clearness upon cooling down and stay clear and stable upon being stored. The achievable storage time (roughly corresponding to the shelf life time of a product) is apparently not limited. In preliminary stability analyses there was no solubilisate according to the invention where the minimum storage time was less than 14 days. In some cases even a storage time of the cosmetic product of minimum 9 months could be assessed (see Exp. 2).

However, for augmenting the shelf life of solubilisates containing at least one oxidation-prone cosmetic agent at least one antioxidant can be added to the solubilisate. In preferred embodiments this at least one antioxidant is a cosmetically acceptable excipient. Suitable antioxidants can be selected from the group comprising lactic acid, ascorbic acid, sodium ascorbate, calcium ascorbate, potassium ascorbate, fatty acid esters of ascorbic acid, ascorbyl palmitate, ascorbyl stearate, tocopherols, alpha-tocopherol, beta-tocopherol, gamma-tocopherol, delta-tocopherol, alpha-tocotrienol, beta-tocotrienol, gamma-tocotrienol, delta-tocotrienol, propyl gallate, octyl gallate, dodecyl gallate, ethyl gallate, guaiac resin, erythorbic acid, sodium erythorbate, erythorbin acid, sodium erythorbin, tert-butylhydroquinone, butylated hydroxyanisole, butylated hydroxytoluene, mono-, di-, trisodium phosphate, mono-, di-, tripotassium phosphate, anoxomer, ethoxyquin, potassium lactate, stannous chloride, sodium thiosulfate, 4-hexylresorcinol, glucose oxidase. Preferred are ascorbyl palmitate and alpha-tocopherol, beta-tocopherol, gamma-tocopherol, delta-tocopherol. Particularly preferred is a combination of ascorbyl palmitate and at least one of alpha-tocopherol, beta-tocopherol, gamma-tocopherol, delta-tocopherol.

According to the method of the invention this at least one antioxidant can be optionally added to said solubilisate or its preferred embodiments in the overall range of 0.01% to 10% per weight, preferred 0.1% to 5% per weight, more preferred 0.2% to 1% per weight and most preferred 0.3% to 0.5% per weight.

Thus the present application refers also to the solubilisate resulting from the solubilizing method according to the invention:

A solubilisate of at least one cosmetic agent, comprising: at least one cosmetic agent in the range of 0.5% to 25% per weight and the following solubilization agents:
  a) at least one phosphatidylcholine in the overall range of 20% to 80% per weight;
  b) at least one medium-chained triglyceride in the overall range of 10% to 70% per weight;
  c) at least one lysophosphatidylcholine in the overall range of 1% to 15% per weight;
  d) at least one $C_2$ to $C_4$ alcohol in the overall range of 1% to 20% per weight, and
  e) and at least one of glyceryl stearate or a saturated or unsaturated $C_{14}$ to $C_{20}$ fatty acid in the range of 0.5% to 10% per weight, respectively,
wherein the relative weight percentages of all ingredients add up to 100% and all solubilization agents are independently from one another cosmetically acceptable excipients.

In a preferred embodiment the solubilisate according to the invention comprises at least one cosmetic agent in the range of 2% to 15% per weight and
  a) at least one phosphatidylcholine in the overall range of 40% to 70% per weight;
  b) at least one medium-chained triglyceride in the overall range of 20% to 40% per weight;
  c) at least one lysophosphatidylcholine in the overall range of 3% to 8% per weight;
  d) at least one $C_2$ to $C_4$ alcohol in the overall range of 2% to 10% per weight, and
  e) and at least one of glyceryl stearate or a saturated or unsaturated $C_14$ to $C_{20}$ fatty acids in the range of 0.5% to 5% per weight, respectively,
wherein the relative weight percentages of all ingredients add up to 100% and all solubilization agents are independently from one another cosmetically acceptable excipients.

In a further preferred embodiment the solubilisate according to the invention comprises at least one cosmetic agent in the range of 5% to 10% per weight and
  a) at least one phosphatidylcholine in the overall range of 40% to 60% per weight;
  b) at least one medium-chained triglyceride in the overall range of 25% to 35% per weight;
  c) at least one lysophosphatidylcholine in the overall range of 5% to 7% per weight;
  d) at least one $C_2$ to $C_4$ alcohol in the overall range of 4% to 7% per weight, and
  e) and at least one of glyceryl stearate or a saturated or unsaturated $C_{14}$ to $C_{20}$ fatty acids in the range of 0.5% to 5% per weight, respectively,
wherein the relative weight percentages of all ingredients add up to 100% and all solubilization agents are independently from one another cosmetically acceptable excipients.

It should be pointed out that a solubilisate according to the invention is free of water. Thus, all solubilisates according to the invention are characterized by being free of water.

Further, a solubilisate according to the invention is free of glycol. Thus, all solubilisates according to the invention are characterized by being free of glycol.

Further, a solubilisate according to the invention is free of urea. Thus, all solubilisates according to the invention are characterized by being free of urea.

The term "cosmetic preparation" or "cosmetic composition" as used in the present application refers to cosmetic compositions as defined under the heading "Kosmetika" in Römpp Lexikon Chemie, 10th edition 1997, Georg Thieme Verlag Stuttgart, New York. Skin and hair cleaning compositions are also included in the cosmetic compositions of the invention.

A "cosmetic agent" according to the invention is defined as a substance included in a cosmetic preparation having a physical, physicochemical, chemical, biochemical and/or subject-related effect under application conditions, thus influencing the physiology and/or function of the skin or mucosa and their adnexae, the teeth or the hair, under exclusion of a substantial systemic effect on the organism (cf. Umbach (1985) Kosmetik and Hygiene, Wiley-VCH). Therefore different regulatory requirements exist for cosmetic agents in almost all countries. According to the invention, these cosmetic products containing an inventive solubilisate of at least one cosmetic agent shall be used exclusively for cosmetic purposes in substantially healthy persons. Any possible therapeutic use in a patient in need thereof shall not be covered by the term cosmetic agent.

The term "cosmetically acceptable excipient" refers to substances that are added to cosmetic preparations. They have to be compatible with the skin, the lips, the nail, the scalp, the hair, the eyelashes, the eyebrows and mucous membranes, should have a pleasant color, odor and feel and should not give rise to unacceptable discomfort liable to discourage the consumer from using this composition, or even put consumers' health at jeopardy. They can preserve the odor or enhance the optical appearance, bestow chemical, physical or galenic advantages to the cosmetic product through control of its consistency, odor, color, skin feel, chemical and microbiological durability, for increasing their practical usage value or for ensuring efficient cosmetic production. They can be synthetic compounds or of natural origin. In virtually all countries they are strictly regulated.

According to the invention said solubilisate or its preferred embodiments may additionally contain an antioxidant as listed before in the overall range of 0.01% to 10% per weight, preferred 0.1% to 5% per weight, more preferred 0.2% to 1% per weight and most preferred 0.3% to 0.5% per weight.

In a particularly preferred embodiment of this solubilisate said at least one saturated or unsaturated $C_{14}$ to $C_{20}$ fatty acid is oleic acid.

In a particularly preferred embodiment of this solubilisate said at least one $C_2$ to $C_4$ alcohol is ethanol.

In preferred embodiments, at least one antioxidant in the overall range of 0.01 to 10% per weight is added to the solubilisate in step b) of the method according to the invention, wherein said at least one antioxidant is a cosmetically acceptable excipient.

In particularly preferred embodiments said at least one antioxidant is ascorbyl palmitate and/or at least one tocopherol.

According to the invention the compound to be solubilized is a cosmetic agent. Thus all cosmetic agents can be solubilized by the method according to the invention. The inventive method is particularly suitable for the solubilization of poorly water-soluble cosmetic agents. Poor water solubility of a cosmetic agent often coincides with poor skin penetration when administered in an aqueous formulation. When applied in a lipophilic cosmetic base lipophilic cosmetic agents solved therein use to have a better skin permeability than hydrophilic compounds.

The solubilisate according to the invention can be used in virtually any cosmetic base, regardless of its nature.

Thus the present application refers also to the solubilisate according to the invention for use in a cosmetic preparation comprising a lipophilic cosmetic base.

Thus the present application refers also to the solubilisate according to the invention for use in a cosmetic preparation comprising a hydrophilic cosmetic base.

Herein the term skin permeability refers to the extent of absorption of a cosmetic agent in the human skin, above all the absorption through the stratum corneum. It corresponds to the flux (absorption rate) of the cosmetic agent across the stratum corneum barrier. It defines the quantity or fraction of the applied dose that is absorbed per time interval. It can be expressed as the diffusion distance overcome by a cosmetic agent in the skin per time. According to the invention a cosmetic agent shall be qualified as having a poor skin permeability when the skin permeability coefficient is $\leq 10^{-7}$ cm/s, and as having a good skin permeability when the skin permeability coefficient is $>10^{-7}$ cm/s.

Transdermal delivery is a passive process governed by Fick's law. The flux across the barrier is proportional to its concentration difference across that barrier. Thus the flux is an estimate of the topical bioavailability of a cosmetic compound in the skin layers. The flux is defined as the absorbed amount of the cosmetic agent per time and area.

$$J = \frac{D}{\Delta x} * K_{skin/vehicle} * C_{vehicle}$$

(J: flux; D=diffusivity; $\Delta x$=diffusion path-length; $K_{skin/vehicle}$=compound's partition coefficient between skin and vehicle; $C_{vehicle}$=compound's soluble amount (solubility) in vehicle)

The term $$\frac{D}{\Delta x} * K_{skin/vehicle}$$

is subsumed as permeability coefficient $k_p$.

$k_p$ is not always easy to assess. Therefore the following approximation according to Potts and Guy (1992, Pharm Res 9, p. 663-669) is frequently used:

$$\log k_p = -2.7 + 0.71 * \log P - 0.0061 * MW$$

(P=octanol-water partition coefficient of the compound; MW=molecular weight).

For highly lipophilic compounds the Cleek & Bunge correction is often applied:

$$k_p^{corr} = \frac{k_p}{1 + \frac{k_p * \sqrt{MW}}{2.6}}$$

Thus for calculating a good estimate of the flux of a cosmetic agent the octanol-water partition coefficient kp of the compound has to be determined, its molecular weight MW has to be known and its soluble amount in vehicle $C_{vehicle}$ has to be assessed.

As kp and MW are intrinsic features of a compound, the flux and thus the dermal bioavailability can only be improved by increasing the solubility of the compound. As it can be assumed from the Experiments, the method according to the invention is apt to solubilize a lipophilic cosmetic agent to virtually 100%. The solubilisate is also completely solved in the respective cosmetic vehicle (=cosmetic base). Therefore, $C_{vehicle}$ can be approximately taken as the amount of the cosmetic agent that was provided in the first place for solubilization. This yields a good estimate for the flux. Vice versa, if it is known which flux is necessary to achieve the desired cosmetic effect it can be calculated back which amount of the cosmetic agent should be roughly provided for solubilization.

It is advantageous for a good skin permeability that the solubilisate containing a poorly water-soluble organic cosmetic agent is in a liquid crystalline state. This is achieved by the solubilisates generated by the solubilization methods disclosed herein.

Thus the present application refers also to the solubilisate according to the invention for use in a cosmetic preparation, wherein at least one cosmetic agent is solubilized in said solubilisate.

In one embodiment the cosmetic agent to be solubilized is provided in the form of a plant extract. This extract can be solubilized likewise by the method of the invention.

In preferred embodiments bioperine (piperine, an extract from black pepper) can be added to further increase skin penetration of the solubilized cosmetic agent.

Thus the present application refers also to the solubilisate according to the invention for use in a cosmetic preparation, containing additionally bioperine.

In cosmetics, bioavailability (also: cutaneous bioavailability; skin bioavailability) is defined as the degree to which a cosmetic agent becomes available to the target tissue after administration.

In a preferred embodiment of the invention cosmetic agents having a poor solubility in water-based preparations are used for the production of a solubilisate.

In a preferred embodiment of the invention lipophilic cosmetic agents having a poor skin permeability as defined above when applied in an aqueous formulation are used for the production of a solubilisate.

In a particularly preferred embodiment of the invention lipophilic cosmetic agents having a poor solubility as well as a poor skin permeability as defined above when applied in an aqueous formulation are used for the production of a solubilisate.

Examples for poorly water-soluble organic cosmetic agents, without being limiting, are: Farnesol, geraniol, geranyl geraniol, dibutyl phthalate, dimethylphenyl butanol, ubiquinones such as coenzyme Q10, thymol, oryzanol, butyl methoxydibenzoyl methane, bis-ethylhexyl cyclophenol, methoxyphenol triazine, menthol, retinol, retinyl esters, retinoic acid, retinyl propionate, retinol palmitate, lutein esters, nicotinate tocopherol, tocopherols, tocopheryl acetate, vitamins D, F, H, K, PP, allantoin, acetylglucosamine, madecassic acid, asiaticoside and asiatic acids, ellagic acid, salicylic acid, ethylhexyl salicylate, stigmasterol, sitosterol, campesterol, brassicasterol, teprenone, genistein, equol, hexamidine, dimethylaminoethanol (DMAE), oils containing DHA/EPA, shea butter, glycerin, oridonine, palm stearic acid, clotrimazole, crotonates copolymer, hexadecane copolymer, VA copolymer, camphor, 4-methylbenzylidene camphor, chlorhexidine, butyl hydroxy toluene, carotenoids, lycopene, triclosan, kojic acid, eucalyptol, polylactic acid, squalene, squalane, trimyristin, tripalmitin, benzophenone-3, benzophenone-4, benzophenone-5, butyl methoxydibenzoylmethane, bis-ethyl-hexyloxyphenol methoxyphenyl triazine, methylene bis-benzotriazolyl tetramethylbutylphenol, diethylamino hydroxybenzoyl hexyl benzoate, diethylhexyl butamido triazone, drometrizole trisiloxane, ethylhexyl triazone (octyltriazone), homosalate, isoamyl p-methoxycinnamate, octocrylene, octinoxate, octisalate, p-aminobenzoic acid (PABA), phenylbenzimidazole sulfonic acid, polysilicone-15, alpha-bisabolol, caprylic/capric triglyceride, decyl oleate, cinoxate, octyldimetyl PABA (Pamidate O), dioxybenzone, resveratrol, 2-ethylhexyl stearate, ethylhexyl glycerin, stearyl ether, propylheptyl caprylate, amodimethicone, behenoxy dimethicone, cyclohexasiloxane, cyclomethicone, cyclotertrasiloxane, stearoxy dimethicone, cetearyl methicone, cetyl dimethicone, cyclopentasiloxane, dimethicone, dimethiconol, phenyl trimethicone, stearyl dimethicone, trimethylsilylamodimethicone, 2-mercaptobenzothiazole.

Moreover, specific plant extracts are often used as cosmetic agents. Many substances generated in the plant secondary metabolism are lipophilic. Examples include extracts from *Persea gratissima* (avocado), *Persea americana* (avocado), *Fucus vesicolosus* (bladder wrack), *Hamamelis virginiana* (witch hazel), *Chamomilla recutita* (=*Matricaria chamomilla*; chamomile), cotton seed oil, *Simmondsia chinensis* (jojoba), *Glycyrrhiza glabra* (liquorice), *Satureja montana* (winter savory), *Arnica montana* (*Arnica*), *Aspalathus linearis* (rooibos tea), *Azadirachta indica* (neem oil), *Camellia sinensis* (green tea), *Cananga odorata* (ylang ylang), *Citrus aurantifolia* (lime), *Citrus bergamia* (Italian bergamot), *Cocus nucifera* (virgin coconut oil), *Cymbopogon citratus* (Indian lemongrass), *Daucus carrota* (carrot), *Eucalyptus globulus* (*Eucalyptus*), Glycine soja (soybean), *Heliantius annuus* (sunflower), Lavendula hybrid (lavender), *Melaleuca alternifolia* (tea tree), *Melaleuca ericifolia* essential oil, *Leptospermum petersonii* essential oil, *Mentha piperita* (peppermint), *Melissa officinalis* (lemon balm, balm mint), *Mentha spicata* (spearmint), palm oil, *Prunus dulcis* (almond), *Prunus persica* (peach), *Rosa damascene* (rose), *Rosa mosqueta* (rosehip), *Rosmarinus officinalis* (rosemary), *Salix nigra* (black willow) bark, *Salvia sclarea* (French clary sage), *Salvia officinalis* (sage), *Sesamum indicum* (sesame), *Stelaria media* (wild harvested chickweed), *Symphytum officinale* (comfrey), *Triticum vulgare* (wheat germ), *Zinziber officinale* (Madagascar ginger), *Borago officinalis* (borage), *Aloe vera* (=*Aloe barbadensis*), *Juglans regia* (walnut), *Butyrospermum parkii* (=*Vitellaria paradoxa*; shea tree), *Dioscorea* spec., in particular *Dioscorea villosa* (wild yam), *Garcinia cambogia* (*Garcinia*, monkey fruit), *Calophyllum inophyllum* (tamanu oil), *Rhamnus* spec. (buckthorn oil), sallow thorn oil, *Physalis pubescens* (husk tomato), *Chondrus crispus* (Irish moss), *Erythrina edulis* (basul tree) seeds, *Phytolacca bogotensis* leaves, *Annona muricata* (guanabana) leaves, *Aloe barbadensis* leaves, *Porphyridium cruentum* (red algae), *Tibouchina lepidota*, *Myrciaria dubia* (camu camu) fruits, *Euterpe precatoria* fruits, *Calendula* spec. (marigold), *Tilia* spec. (linden, lime tree), *Vitis* spec. (grape) seeds, *Hedera* spec. (ivy), *Arctostaphylos* spec. (bearberry), *Betula* spec. (birch), *Achillea millefolium* (yarrow), *Panax* spec. (ginseng), *Cucumis sativus* (cucumber), *Boswellia* spec. (frankincense), algae.

Some of the aforementioned cosmetic agents are also available as a salt which is mostly dissociated at a physiological pH. In general, these salts don't need a solubilization for use in an aqueous finished solution. However, a solubilization according to a method according to the invention can improve e.g. the skin permeability. However, a solubilization of such dissociated salts works less well with a method according to the invention than the solubilization of the respective base, as these salts are normally only slightly soluble in oil, if at all. Moreover, their electric charge impairs a self-emulsification during the solubilization process according to the invention. It was found that maximally 2 weight-% of salts of organic cosmetic agents can be solved according to the inventive method.

Thus, in preferred embodiments the solubilization methods and the solubilisates according to the invention are further characterized in that they are free of salts having a $pK_a$ value <4.

Thus, the present application refers also to a solubilisate according to the invention for use in a cosmetic preparation, wherein the at least one cosmetic agent solubilized in said solubilisate is a specific plant extract.

Moreover, the present application refers also to the use of the solubilisate according to the invention in cosmetics in a cosmetic product.

As laid out before, one goal of the solubilisate according to the invention is to enable an augmented skin permeability and/or dermal bioavailability of the cosmetic agent solubilized in said solubilisate. Thus, the present application refers also to a solubilisate according to the invention, in which the solubilisate of the at least one cosmetic agent enhances the skin permeability and/or dermal bioavailability of at least one of said cosmetic agents.

A further aspect of the invention is that some cosmetic agents intrinsically have an unpleasant odor, sometimes due to oxidation processes. This is often a serious commercialization obstacle for a cosmetic product containing such a cosmetic agent. A solubilisate according to the invention can significantly help to mask this unpleasant odor by caging the substance upon solvation in a cosmetic base. The solubilisates according to the invention use to have a neutral odor, likewise the cosmetic preparation containing a solubilisate according to the invention.

Thus the present invention relates also to a solubilisate of a cosmetic agent or to a cosmetic preparation containing such a solubilisate in which an unpleasant odor of the cosmetic agent is masked by the solubilisate prepared by the method according to the invention.

Examples of cosmetic agents with an unpleasant, foul or pungent odor comprise, without being limiting, monoethanolamine, dihydroxyacetone, glutathione, hydroquinone, mercapto compounds such as hetero-aryl-mercapto-alkanoic acid derivatives, mercapto-functional silicones, mercapto-carboxylic acids, 2-mercaptobenzothiazole, thioglycolic acid, ammonium thioglycolate and glyceryl monothioglycolate, ammonium , amino compounds such as spermine and spermidine, polyether-modified silicones such as dimethicone, amodimethicone, behenoxy dimethicone, cyclohexasiloxane, cyclomethicone, cyclotertrasiloxane, stearoxy dimethicone, cetearyl methicone, cetyl dimethicone, cyclopentasiloxane, dimethiconol, phenyl trimethicone, stearyl dimethicone, trimethylsilylamodimethicone, extracts from *Physalis pubescens* (husk tomato), *Chondrus crispus* (Irish moss), *Erythrina edulis* (basul tree) seeds, *Phytolacca bogotensis* leaves, *Annona muricata* (guanabana) leaves, *Aloe barbadensis* leaves, *Porphyridium cruentum* (red algae), *Tibouchina lepidota*, *Myrciaria dubia* (camu camu) fruits, *Euterpe precatoria* fruits, *Matricaria chamomilla* (chamomile), *Azadirachta indica* (neem oil), *Calophyllum inophyllum* (tamanu oil), *Rhamnus* spec. (buckthorn oil).

In a preferred embodiment the solubilisate according to the invention contains a cosmetic agent with a poor skin permeability and/or dermal bioavailability when applied in an aqueous formulation, and with an unpleasant odor. Suitable examples comprise, without being limiting, polyether-modified silicones such as dimethicone, amodimethicone, behenoxy dimethicone, cyclohexasiloxane, cyclomethicone, cyclotertrasiloxane, stearoxy dimethicone, cetearyl methicone, cetyl dimethicone, cyclopentasiloxane, dimethiconol, phenyl trimethicone, stearyl dimethicone, trimethylsilylamodimethicone, extracts from *Physalis pubescens* (husk tomato), *Chondrus crispus* (Irish moss), *Erythrina edulis* (basul tree) seeds, *Phytolacca bogotensis* leaves, *Annona muricata* (guanabana) leaves, *Aloe barbadensis* leaves, *Porphyridium cruentum* (red algae), *Tibouchina lepidota, Myrciaria dubia* (camu camu) fruits, *Euterpe precatoria* fruits, *Matricaria chamomilla* (chamomile), *Azadirachta indica* (neem oil), *Calophyllum inophyllum* (tamanu oil), *Rhamnus* spec. (buckthorn oil).

In most cases, the solubilisate itself is not yet a cosmetic preparation or a cosmetic product. To be ready for application the solubilisate is solved in a cosmetic base. Suitable containers for a cosmetic base with a solubilisate according to the invention can be selected from a group comprising bottles, flacons, glasses, cups, jars, pots, dispensers, boxes, tubes, caps, syringes, sachets, flasks, vials, custom-built two- or multiple-compartment containers.

Thus the present application refers also to a cosmetic preparation, wherein the solubilisate according to the invention is solved in a cosmetic base. Optionally, cosmetic excipients as disclosed herein can be added. The term "cosmetic base" refers to a composition which serves as a matrix for the at least one cosmetic agent, in the present case for the solubilisate according to the invention containing at least one cosmetic agent. The cosmetic preparation according to the invention can be portioned and packed in suitable containers. Said containers filled with a cosmetic preparation according to the invention are referred to as a cosmetic product.

A cosmetic base can be prepared from suitable agents belonging among others to the groups of additional emulsifiers, film formers, gel formers, additional solvents, oil components, agents for a soap base, thickeners/consistency enhancers and waxes.

Additional emulsifiers can be selected for example from the following anionic and non-ionic emulsifiers: Anionic emulsifier waxes, cetyl alcohol, cetylstearyl alcohol, stearic acid, oleic acid, polyoxyethylene polyoxypropylene block polymers, addition products of 2 to 60 mol ethylene oxide to castor oil and/or hardened castor oil, wool wax oil (lanolin), sorbitan esters, polyoxyethylene alkyl esters, polyoxyethylene sorbitan fatty acid esters, polyoxyethene sorbitan monolaurate, polyoxyethene sorbitan monooleate, polyoxyethene sorbitan monopalmitate, polyoxyethene sorbitan monostearate, polyoxyethene sorbitan tristearate, polyoxyethene stearate, polyvinyl alcohol, metatartaric acid, calcium tartrate, alginic acid, sodium alginate, potassium alginate, potassium cetyl phosphate, potassium stearate, ammonium alginate, calcium alginate, propane-1,2-diol alginate, carrageenan, processed eucheuma seaweed, locust bean gum, tragacanth, acacia gum, karaya gum, gellan gum, gum ghatti, glucomannane, pectin, amidated pectin, ammonium phosphatides, brominated vegetable oil, sucrose acetate isobutyrate, glycerol esters of wood rosins, disodium phosphate, trisodium diphosphate, tetrasodium diphosphate, dicalcium diphosphate, calcium dihydrogen diphosphate, sodium triphosphate, pentapotassium triphosphate, sodium polyphosphates, sodium calcium polyphosphate, calcium polyphosphates, ammonium polyphosphate, beta-cyclodextrin, powdered cellulose, methyl cellulose, ethyl cellulose, hydroxypropyl cellulose, hydroxypropyl methylcellulose, ethyl methyl cellulose, carboxymethyl cellulose, sodium carboxymethyl cellulose, ethyl hydroxyethyl cellulose, croscarmellose, enzymically hydrolyzed carboxymethyl cellulose, mono- and diglycerides of fatty acids, glyceryl monostearate, PEG-20 glyceryl stearate, glyceryl distearate, glyceryl oleate, acetic acid esters of mono- and diglycerides of fatty acids, lactic acid esters of mono- and diglycerides of fatty acids, citric acid esters of mono- and diglycerides of fatty acids, tartaric acid esters of mono- and diglycerides of fatty acids, mono- and diacetyl tartaric acid esters of mono- and diglycerides of fatty acids, mixed acetic and tartaric acid esters of mono- and diglycerides of fatty acids, succinylated monoglycerides, sucrose esters of fatty acids, sucroglycerides, polyglycerol esters of fatty acids, polyglycerol polyricinoleate, propane-1,2-diol esters of fatty acids, propylene glycol esters of fatty acids, lactylated fatty acid esters of glycerol and propane-1, thermally oxidized soy bean oil interacted with mono- and diglycerides of fatty acids, dioctyl sodium sulphosuccinate, sodium stearoyl-2-lactylate, calcium stearoyl-2-lactylate, stearyl tartrate, stearyl citrate, sodium stearoyl fumarate, calcium stearoyl fumarate, stearyl tartrate, stearyl citrate, sodium stearoyl fumarate, calcium stearoyl fumarate, sodium laurylsulfate, ethoxylated mono- and diglycerides, methyl glucoside-coconut oil ester, sorbitan monostearate, sorbitan tristrearate, sorbitan monolaurate, sorbitan monooleate, sorbitan monopalmitate, sorbitan trioleate, calcium sodium polyphosphate, sodium stearate, calcium polyphosphate, ammonium polyphosphate, cholic acid, choline salts, distarch glycerol, starch sodium octenyl succinate, acetylated oxidized starch, ceteareth-20, cetearyl glucoside, cetyl PEG/PPG-10/1 dimethicone, cocamide mea, PEG-120 methyl glucose dioleate, PEG 18 glyceryl oleate/cocoate, PEG-7 hydrogenated castor oil, PEG-40 hydrogenated castor oil, PEG-7 glyceryl cocoate, polyglyceryl-3 diisostearate, polyglyceryl-3 methylglucose distearate, polyglyceryl-3 polyricinoleate, polyglyceryl-4 caprylate, propylene glycol dicaprylate/dicaprate, sodium C12-12 pareth sulfate, sodium cetearyl sulfate, steareth-2, steareth-21, sucrose laurate, sucrose myristate, sucrose ricinoleate.

Preferred are glycerin monooleate and stearic acid.

Suitable film formers can be selected from the group comprising, but not limited to, acrylates copolymer, acrylates/hydroxyesters acrylates copolymer, acrylates/steareth-20 methacrylate crosspolymer, dibutyl sebacate, nitrocellulose, polyvinyl pyrrolidone, sodium carbomer, tosylamide/formaldehyde resin.

Suitable gel formers can be selected from the group comprising, but not limited to, agar, algin, alginic acid, bentonite, carbomer, carrageenan, hectorite, hydroxyethyl cellulose, hydroxypropyl cellulose, polyvinyl alcohol, polyvinyl pyrrolidone, sodium carbomer.

Suitable additional solvents may be selected from the group comprising water, carbonated water, water for injection, water with isotonizing agents, saline, isotonic saline, alcohols, particularly ethyl, isopropyl and n-butyl alcohol, denaturized alcohol, oleic and linoleic acid triglycerides, acetone, glycerin, caprylic and capric acid mono-, di- and triglycerides, polyoxyethylene caprylic and capric acid glycerides, low alkyl fatty acid esters, soy bean oil, polyoxyethylene (35) castor oil, polyoxyethylene glyceryl trioleate, ethyl butyrate, ethyl caprylate, ethyl oleate, ethyl acetate, butyl acetate, cyclopentasiloxane, and mixtures thereof.

Suitable oil components can be selected from the group comprising, but not limited to, caprylic/capric triglyceride, cetearyl alcohol, cyclomethicone, dibutyl sebacate, dicaprylyl ether, diisodecyl adipate, dimethicone, glyceryl stearate, isopropyl myristate, isopropyl palmitate, macadamia integrifolia seed oil, macadamia ternifolia seed oil, octyldodecanol, paraffin, paraffinum liquidum, persea gratissima oil, simmondsia chinensis seed oil, stearic acid.

Suitable agents for a soap base can be selected from the group comprising, but not limited to, potassium stearate, sodium cocoate, sodium olivate, sodium palmate, sodium palmitate, sodium stearate.

Suitable thickeners or consistency enhancers can be selected from the group comprising, but not limited to, acrylates polymer, acrylates/C10-30 alkyl acrylate crosspolymer, agar, ammonium alginate, amylopectin, carrageenan, cellulose, cellulose gum, cocamide mea, glyceryl stearate, hydrated silica, PEG-150 distearate, polyvinyl alcohol, potassium chloride, sodium acrylates copolymer, sodium chloride, VP/hexadecane copolymer, xanthan gum.

Suitable waxes can be selected from the group comprising, but not limited to, candelilla cera, cera alba, cera microcristallina, ceresin, copernicia cerifera cera, lanolin cera, ozokerite, simmondsia chinensis seed cera.

Moreover, the present application refers also to a cosmetic preparation containing at least one cosmetic agent formulated in a solubilisate according to the invention and at least one cosmetically acceptable excipient.

The term "cosmetically acceptable excipient" refers to natural or synthetic compounds that are added to a cosmetic preparation alongside the cosmetic agent. They may be added to the solubilisate produced according to the invention, and/or to a cosmetic base which serves as a matrix for a solubilisate according to the invention. Advantageous classes of cosmetically acceptable excipients, respectively adjuvants or additives according to the invention include acidifiers, alkalization agents and neutralization agents, additional antioxidants, binding agents, colorants, pigments or nanopigments, e.g. those suited for providing a photoprotective effect by physically blocking out ultraviolet radiation, moisturizers/humectants, resins, preservatives, oxidizing agents, reducing agents, stabilizers, opacifiers or pearl shine pigments, denaturants, plasticizers, fragrances, surfactants, diluents, fillers, additional solubilizers, penetration enhancers, or any other excipients usually formulated in cosmetic products.

pH regulation is essential for the efficacy and stability of cosmetic products. Suitable acidity regulators, acidifiers, alkalization agents and neutralization agents can be selected from the group comprising acetic acid, hydrochloric acid, aminomethyl propanol, ammonia, ammonium bicarbonate, potassium acetate, sodium acetate, sodium diacetate, calcium acetate, carbon dioxide, malic acid, fumaric acid, sodium lactate, sodium bicarbonate, sodium metaphosphate, sodium trimetaphosphate, sodium phosphate, potassium lactate, calcium lactate, ammonium lactate, magnesium lactate, citric acid, mono-, di-, trisodium citrate, mono-, di-, tripotassium citrate, mono-, di-, tricalcium citrate, tartaric acid, mono-, disodium tartrate, mono-, dipotassium tartrate, sodium potassium tartrate, disodium phosphate, disodium pyrophosphate, ortho-phosphoric acid, lecithin citrate, magnesium citrate, ammonium malate, sodium malate, sodium hydrogen malate, calcium malate, calcium hydrogen malate, adipic acid, sodium adipate, potassium adipate, ammonium adipate, succinic acid, sodium fumarate, potassium fumarate, calcium fumarate, ammonium fumarate, 1,4-heptonolactone, triammonium citrate, ammonium ferric citrate, calcium glycerophosphate, calcium chloride, isopropyl citrate, potassium carbonate, potassium bicarbonate, potassium phosphate, tetrapotassium pyrophosphate, ammonium carbonate, magnesium carbonate, magnesium bicarbonate, ferrous carbonate, ammonium sulfate, aluminium potassium sulfate, aluminium ammonium sulfate, sodium hydroxide, potassium hydroxide, ammonium hydroxide, ammonium chloride, magnesium hydroxide, gluconic acid, ethanolamine, triethanolamine.

Additional suitable antioxidants can be selected from the group comprising lactic acid, ascorbic acid, sodium ascorbate, calcium ascorbate, potassium ascorbate, fatty acid esters of ascorbic acid, ascorbyl palmitate, ascorbyl stearate, tocopherols, alpha-tocopherol, gamma-tocopherol, delta-tocopherol, tocopheryl acetate, propyl gallate, octyl gallate, dodecyl gallate, ethyl gallate, guaiac resin, erythorbic acid, sodium erythorbate, erythorbin acid, sodium erythorbin, tert-butylhydroquinone, butylated hydroxyanisole, butylated hydroxytoluene, mono-, di-, trisodium phosphate, mono-, di-, tripotassium phosphate, anoxomer, ethoxyquin, potassium lactate, stannous chloride, sodium thiosulfate, 4-hexylresorcinol, glucose oxidase, carotenoids, lycopene, ubiquinone.

The term tocopherol refers to any of the aforementioned tocopherols or a mixture thereof.

The term binding agents refers to substances that bind powders or glue them together, rendering them cohesive through granule formation. They serve as a "glue" of the preparation. Binding agents increase the cohesive strength of the provided diluent or filler.

Suitable binding agents are for example acacia, agar, alginic acid, amylopectin, behenyl alcohol, benzoin gum, calcium caseinate, carboxymethylcellulose sodium, ceresin wax, collodion, corn starch, croscarmellose sodium, damar gum, dextran, dextrin, ethylcellulose, gelatin, gluten, glycerin, guar gum, hydroxyethyl cellulose, hydroxypropyl cellulose, hypromellose, isopropyl myristate, karaya gum, locust bean gum, maltodextrin, mannitol, mastic gum, methylcellulose, Multiwax®, n-octyltriethoxysilane, VP/VA copolymer, pectin, polyacrylamide, poly(styrene-co-maleic anhydride), polyvinyl acetate, polyvinyl alcohol, polyvinyl butyral, povidone K-30, povidone K-90, polyvinyl pyrrolidone, polyvinyl methyl ether), pullulan, rosin gum, shellac gum, sodium alginate, sodium starch glycolate, sorbitol, potato starch, wheat starch, stearyl palmitate, beeswax, beeswax substitute, tragacanth, tridecafluoro-1,1.2,2-tetrahydrooctyl-1-triethoxysilane, 3-(trimethoxysilyl)propyl methacrylate, white wax, yellow wax, beeswax beads, xanthan gum, and others.

The percentage of the binding agent in the cosmetic preparation according to the invention can range from 1-30% by weight, preferred 2-20% by weight, more preferred 5-15% by weight, most preferred, 10-15% per weight.

Colorants (pigments, dyestuff) are excipients that bestow a colorization to a cosmetic preparation or cosmetic product. Examples therefor include, but are not limited to, inorganic pigments, organic pigments, lakes, pearlescent pigments, iridescent or optically variable pigments, and mixtures thereof. A pigment should be understood to mean inorganic or organic, white or colored particles. The pigments may optionally be surface-treated within the scope of the present invention but are not limited to treatments such as silicones, perfluorinated compounds, lecithin, and amino acids.

Representative examples of inorganic pigments useful in a cosmetic preparation according to present invention include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on Cochineal Carmine (CI 75,570) and mixtures thereof.

Representative examples of pearlescent pigments include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

Further examples of colorants or pigments include Acid Red 195, aluminum stearate, anthocyanins, beta vulgaris, bromocresol green, bromothymol blue, calcium stearate, capsanthin, capsorubin, caramel, CI 1006, CI 10020, CI 10316, CI 11680, CI 11710, CI 11725, CI 11920, CI 12010, CI 12085, CI 12120, CI 12370, CI 12420, CI 12480, CI 12490, CI 12700, CI 13015, CI 14270, CI 14700, CI 14720, CI 14815, CI 15510, CI 15525, CI 15580, CI 15620, CI 15630, CI 15800, CI 15850, CI 15865, CI 15880, CI 15980, CI 15985, CI 16035, CI 16185, CI 16230, CI 16255, CI 16290, CI 17200, CI 18050, CI 18130, CI 18690, CI 18736, CI 18820, CI 18965, CI 19140, CI 20040, CI 20470, CI 21100, CI 21108, CI 21230, CI 24790, CI 27755, CI 28440, CI 40215, CI 40800, CI 40820, CI 40825, CI 40850, CI 42045, CI 42051, CI 42053, CI 42080, CI 42090, CI 42100, CI 42170, CI 42510, CI 42520, CI 42735, CI 44045, CI 44090, CI 45100, CI 45190, CI 45220, CI 45350, CI 45370, CI 45380, CI 45396, CI 45405, CI 45410, CI 45430, CI 47000, CI 47005, CI 50325, CI 50240, CI 51319, CI 58000, CI 59040, CI 60724, CI 60725, CI 60730, CI 61565, CI 62570, CI 61585, CI 62045, CI 69800, CI 69825, CI 71105, CI 73000, CI 73015, CI 73360, CI 73385, CI 73900, CI 73915, CI 74100, CI 74160, CI 74180, CI 74260, CI 75100, CI 75120, CI 75125, CI 75130, CI 75135, CI 75170, CI 75300, CI 75470, CI 75810, CI 77000, CI 77002, CI 77004, CI 77007, CI 77015, CI 77120, CI 77163, CI 77220, CI 77231, CI 77266, CI 77266 (nano), CI 77267, CI 77268:1, CI 77288, CI 77289, CI 77346, CI 77400, CI 77480, CI 77489, CI 77491, CI 77492, CI 77499, CI 77510, CI 77713, CI 77742, CI 77745, CI 77820, CI 77891, CI 77947, lactoflavin, magnesium stearate, riboflavin, zinc stearate.

The precise amount and type of colorant or pigment employed in the cosmetic compositions of the present invention will depend on the color, intensity and use of the cosmetic composition and, as a result, will be determined by those skilled in the art of cosmetic formulation.

Suitable pigments according to the present invention may be also UV-A and UV-B filters. Examples of UV-B or broad spectrum screening agents, i.e. substances having absorption maximums between about 290 and 340 nm, which are preferred for combination with the solubilisates of the present invention, are the following organic and inorganic compounds: Acrylates such as 2-ethylhexyl 2-cyano-3,3-diphenylacrylate (octocrylene, PARSOL® 340), ethyl 2-cyano-3,3-diphenylacrylate and the like; camphor derivatives such as 4-methyl benzylidene camphor (PARSOL® 5000), 3-benzylidene camphor, camphor benzalkonium methosulfate, polyacrylamidomethyl benzylidene camphor, sulfo benzylidene camphor, sulphomethyl benzylidene camphor, therephthalidene dicamphor sulfonic acid and the like; cinnamate derivatives such as octyl methoxycinnamate (PARSOL® MCX), ethoxyethyl methoxycinnamate, diethanolamine methoxycinnamate (PARSOL® Hydro), isoamyl methoxycinnamate and the like as well as cinnamic acid derivatives bond to siloxanes; p-aminobenzoic acid derivatives, such as p-aminobenzoic acid, 2-ethylhexyl p-dimethylaminobenzoate, N-oxypropylenated ethyl p-aminobenzoate, glyceryl p-aminobenzoate; benzophenones such as benzophenone-3, benzophenone-4, 2,2', 4,4'-tetrahydroxybenzophenone, 2,2'-dihydroxy-4,4'-dimethoxybenzophenone and the like; esters of benzalmalonic acid such as di-(2-ethylhexyl) 4-methoxybenzalmalonate; esters of 2-(4-ethoxy-anilinomethylene)propandioic acid such as 2-(4-ethoxy anilinomethylene)propandioic acid diethyl ester as disclosed in EP 0895 776; organosiloxane compounds containing benzmalonate groups as disclosed in EP 0358584, EP 0538431 and EP 0709080; drometrizole trisiloxane (Mexoryl XL); pigments such as microparticulated $TiO_2$, and the like, (the term "microparticulated" refers to a particle size from about 5 nm to about 200 nm, particularly from about 15 nm to about 100 nm. The $TiO_2$ particles may also be coated by metal oxides such as e.g. aluminum or zirconium oxides or by organic coatings such as e.g. polyols, methicone, aluminum stearate, alkyl silane. Such coatings are well known in the art.); imidazole derivatives such as e.g. 2-phenyl benzimidazole sulfonic acid and its salts (PARSOL® HS); salts of 2-phenyl benzimidazole sulfonic acid are e.g. alkali salts such as sodium- or potassium salts, ammonium salts, morpholine salts, salts of primary, secondary and tertiary amines like monoethanolamine salts, diethanolamine salts and the like; salicylate derivatives such as isopropylbenzyl salicylate, benzyl salicylate, butyl salicylate, octyl salicylate (NEO HELIOPAN OS), isooctyl salicylate or homomenthyl salicylate (homosalate, HELIOPAN) and the like; triazine derivatives such as octyl triazone (UVINUL T-150), dioctyl butamido triazone (UVASORB HEB), bis ethoxyphenol methoxyphenyl triazine (Tinosorb S) and the like.

Examples of broad spectrum or UV A screening agents include substances having absorption maximums between about 320 and 400 nm, such as dibenzoylmethane derivatives such as 4-tert. butyl-4'-methoxydibenzoyl-methane (PARSOL® 1789), dimethoxydibenzoylmethane, isopropyldibenzoylmethane and the like; benzotriazole derivatives such as 2,2'-methylene-bis-(6-(2H-benzotriazole-2-yl)-4-(1, 1,3,3,-tetramethylbutyl)-phenol (TINOSORB M) and the like; phenylene-1,4-bis-benzimidazolsulfonic acids or salts such as 2,2-(1,4-phenylene)bis-(1H-benzimidazol-4,6-disulfonic acid) (Neoheliopan AP); amino substituted hydroxybenzophenones such as 2-(4-diethylamino-2-hydroxy-benzoyl)-benzoic acid hexylester as disclosed in EP 1046391; pigments such as microparticulated ZnO or $TiO_2$ and the like, as described before.

Suitable humectants or moisturizers can be selected from the group comprising, but not limited to, cyclomethicone, cyclopentasiloxane, glycerin, glyceryl triacetate, lactic acid, PEG-6, sodium lactate, sorbitol, xylitol, maltitol, neoagarobiose, polydextrose, quillaia, *Aloe vera* gel, MP diol, honey, egg yolk, egg white, lithium chloride, sodium hexametaphosphate.

Suitable resins can be selected from the group comprising, but not limited to, polymethacrylic acid, polyvinyl acetate, tosylamide/formaldehyde resin.

Preservatives for cosmetic preparations can be used on demand. They may be selected from the group comprising, but not limited to, phenoxyethanol, benzoate, benzlyl alcohol, alkyl para-hydroxybenzoates, wherein the alkyl radical has from 1, 2, 3, 4, 5 or 6 carbon atoms and preferably from 1 to 4 carbon atoms e.g., methyl para-hydroxybenzoate (methylparaben), ethyl para-hydroxybenzoate(ethylparaben), propyl para-hydroxybenzoate(propylparaben), butyl para-hydroxybenzoate(butylparaben), isobutyl para-hydroxybenzoate(isobutylparaben), calcium paraben, potassium paraben, potassium butylparaben, potassium propylparaben, sodium propylparaben, potassium ethylparaben, potassium methylparaben, sodium butylparaben, sodium ethylparaben, sodium methylparaben, sodium paraben, propylparaben, calcium propionate, calcium salicylate, calcium sorbate, ammonium benzoate, ammonium bisulfite, potassium metabisulfite, sodium bisulfite, sodium metabisulfite, ammonium sulfite, ammonium propionate, 2-bromo-2-nitro-propane-1,3-diol, 4-hydroxybenzoic acid, 5-bromo-5-nitro-1,3-dioxane, stearalkonium chloriode, benzalkonium bromide, benzalkonium chloride, benzethonium chloride, bromochlorophene, phenyl benzoate, butyl benzoate, isobutyl benzoate, isopropyl benzoate, propyl benzoate, ethyl benzoate, methyl benzoate, mea-benzoate, calcium benzoate, magnesium benzoate, potassium benzoate, sodium benzoate, cetrimonium chloride, chiorhexidine, chloroacetamide, chlorobutanol, chlorophene, chlorphenesin, climbazole, dehydroacetic acid, DMDM hydantoin, ethyl lauroyl arginate HCl, formaldehyde, formic acid, sodium formiate, propionic acid, glutaral, hexamidine, iodopropynyl butylcarbamate, isopropyl cresols, magnesium propionate, potassium propionate, sodium propionate, magnesium salicylate, potassium salicylate, sodium salicylate, potassium sorbate, sorbic acid, sodium sorbate, potassium sulfite, sodium sulfite, methylchloroisothiazolinone, methylisothiazolinone, o-phenylphenol, p-chloro-m-cresol, phenoxyethanol, phenoxyisopropanol, piroctone olamine, polyaminopropyl biguanide, triclocarban, triclosan, and their mixtures.

The preservatives may be present in a cosmetic preparation according to the invention in an amount ranging from about 0.01% to about 10% by weight, such as from 0.5% to about 5% by weight, and such as from about 0.8% to about 3% by weight, all weights based on the weight of the composition as a whole.

Suitable oxidizing agents can be selected from the group comprising, but not limited to, ammonium persulfate, hydrogen peroxide, potassium persulfate, sodium persulfate.

Suitable reducing agents can be selected from the group comprising, but not limited to, ammonium bisulfite, ammonium thioglycolate, sodium metabisulfite, thioglycolic acid, thiolactic acid.

Stabilizers are substances that can be added to prevent unwanted changes. Though stabilizers are not real emulsifiers they may also contribute to the stability of emulsions, respectively solubilisates. Suitable examples for stabilizers are oxystearin, xanthan gum, agar, oat gum, guar gum, tara gum, polyoxyethene stearate, aspartame-acesulfame salt, amylase, proteases, papain, bromelain, ficin, invertase, polydextrose, polyvinyl pyrrolidone, polyvinyl polypyrrolidone, triethyl citrate, maltitol, maltitol syrup, cetearyl alcohol, cetyl hydroxymethylcellulose, cocamide mea, disodium EDTA, EDTA, etidronic acid, hydroxymethylcellulose, microcrystalline cellulose, pentasodium pentetate, potassium alginate, sodium carbomer, sodium citrate, sodium gluconate, tetrasodium EDTA, tocopherol, trisodium EDTA.

Suitable opacifiers or pearl shine pigments can be selected from the group comprising, but not limited to, calcium sulfate, cellulose, glycol palmitate, MICA, PEG-2-stearate, propylene glycol distearate, propylene glycol stearate se.

Suitable denaturants can be selected from the group comprising, but not limited to, mint oil, dibutyl phthalate, bis-(2-ethylhexyl) phthalate, bis-(2-methoxyethyl) phthalate, linear or branched dipentyl esters, n-pentyl isopentyl phthalate, di-n-pentyl phthalate, diisopentyl phthalate, benzyl butyl phthalate, phthalic acid and its linear or branched alkyl esters, thymol, denatonium benzoate, tert-butanol, isopropanol, musk ketone.

Suitable plasticizers can be selected from the group comprising, but not limited to, butyl stearate, camphor, cetearyl isononanoate, dibutyl sebacate, dicaprylyl ether, diisodecyl adipate, isopropyl citrate, isopropyl myristate, isopropyl palmitate, octyldodecanol, sorbitol, tosylamide/formaldehyde resin.

Suitable fragrances (aromatic and flavoring substances) comprise above all essential oil that can be used for this purpose. In general, this term refers to volatile extracts from plants or parts of plants with the respective characteristic smell. They can be extracted from plants or parts of plants by steam distillation.

Examples are: Essential oils, respectively aromatic substances from sage, cloves, chamomile, anise, star anise, thyme, tea tree, peppermint, mint oil, menthol, camphor, cineol, *Eucalyptus* oil, mango, figs, lavender oil, chamomile blossoms, pine needles, cypress, oranges, rosewood, plum, currant, cherry, birch leaves, cinnamon, limes, grapefruit, tangerine, juniper, valerian, vanillin, citrus lemon peel oil, lemon balm, lemon grass, palmarosa, cranberry, pomegranate, rosemary, ginger, pineapple, guava, echinacea, rosa indica flower extract, jasmin officinale flower extract, ivy leave extract, blueberry, kaki, melons, etc. or mixtures thereof, as well as mixtures of menthol, peppermint and star anise oil or menthol and cherry flavor, as well as benzyl alcohol, methyl phenylbutanol.

These fragrances can be included in a cosmetic preparation according to the invention in the range of 0.0001 to 10% per weight, preferred 0.001 to 6% per weight, more preferred 0.001 to 4% per weight, most preferred 0.01 to 1% per weight, with regard to the total composition. Application- or single case-related it may be advantageous to use differing quantities.

A cosmetic preparation according to the invention may be in the form of an emulsion which may contain surfactants or a mixture thereof. Suitable surfactants for use in a cosmetic preparation according to the present invention in the form of an emulsion include anionic, nonionic, amphoteric and cationic surfactants.

Suitable anionic surfactants useful in a cosmetic preparation according to the invention may include, but are not limited to, C16-C30 fatty acids neutralized by amines, ammonia or the alkali metal salts thereof.

Suitable nonionic surfactants may include, but are not limited to, fatty acids, fatty alcohols, polyethoxylated fatty alcohols or polyglycerolated fatty alcohols, such as polyethoxylated stearyl alcohols or cetylstearyl alcohols, esters of fatty acid and sucrose, and glucose alkyl esters, in particular polyoxyethylenated C1-C6 alkyl glucose fatty esters.

Suitable amphoteric surfactants may include, but are not limited to, betaines, sultaines, hydroxysultaines, alkyl amphodiacetates, alkyl amphodipropionates, and imidazolines, or salts thereof. Other fatty acid condensates such as those formed with amino acids, proteins, and the like are suitable as well. Specific examples may include cocoamphodipropionate, e.g., "Miranol C2M-SF®" (disodium cocoamphodipropionate), in its salt-free form, and "Crosultaine C-50®" (cocamidopropyl hydroxysultaine).

Suitable cationic surfactants may include, but are not limited to, quaternary amines, amine oxides and amines, e.g., alkyl amines, alkyl imidazolines, ethoxylated amines, quaternary compounds, and quaternized esters.

Surfactants may be present in the cosmetic preparation according to the invention in an amount ranging from about 1% to about 30% by weight, such as from about 5% to about 15% by weight, all weights based on the weight of the composition as a whole.

Diluents or fillers are inactive substances added to cosmetic preparations in order to handle minimal amounts of active agents. They can be useful in the solubilizing process. Examples for suitable diluents are water, mannitol, pregelatinized starch, starch, microcrystalline cellulose, powdered cellulose, silicified microcrystalline cellulose, dibasic calcium phosphate dihydrate, calcium phosphate, calcium carbonate, hydroxypropyl cellulose, hydroxyethyl cellulose, hydroxypropyl methylcellulose, polyethylene glycol, xanthum gum, gum arabic or any combination thereof.

Suitable fillers in a cosmetic preparation according to the invention include, but are not limited to, silica powder; talc; polyamide particles such as Orgasol®; polyethylene powders; microspheres based on acrylic copolymers, such as Polytrap®; expanded powders such as hollow microspheres such as Expancel® or Micropearl F 80 ED®; powders of natural organic materials such as crosslinked or noncrosslinked corn starch, wheat starch or rice starch, such as the powders of starch crosslinked with octenyl succinate anhydride (Dry-Flo®); silicone resin microbeads such as Tospearl®; clays (bentone, laponite, saponite, etc.) and mixtures thereof.

The fillers may be present in a cosmetic preparation according to the invention in an amount ranging from about 0.1% to about 50% by weight, such as from 0.5% to about 30% by weight, and such as from about 1% to about 20% by weight, all weights based on the weight of the composition as a whole.

Suitable as additional surface-active solubilizing agents (solubilizers) are for example diethylene glycol monoethyl ester, polyethyl propylene glycol co-polymers, cyclodextrins such as α- and β-cyclodextrin, glyceryl monostearates such as Solutol HS 15 (Macrogol-15-hydroxystearate from BASF, PEG 660-15 hydroxystearates), sorbitan esters, polyoxyethylene glycol, polyoxyethylene sorbitanic acid esters, polyoxyethylene sorbitan monooleate, polyoxyethylene oxystearic acid triglyceride, polyvinyl alcohol, sodium dodecyl sulfate, (anionic) glyceryl monooleates etc.

Penetration enhancers are chemical substances that temporarily diminish the barrier of the skin and promote or accelerate the absorption of cosmetic agents. The solubilisates according to the invention provide enhanced skin penetration properties. This effect can be further augmented by adding an additional penetration enhancer to a solubilisate according to the invention and/or its cosmetic base. Suitable penetration enhancers can be selected from the group comprising, but not limited to, dimethyl isosorbide (Arias®), dimethyl sulphoxide (DMSO) and its analogues, dimethyl formamide (DMF), azone (1-dodecylazacycloheptan-2-one), pyrrolidones such as 2-pyrrolidone, fatty acids such as oleic acid, lauric acid, myristic acid and capric acid, nonic surfactants such as polyoxyethylene-2-oleyl ether and polyoxyethylene-2-stearyl ether, terpenes, terpenoids and sesquiterpenes such as those from essential oils of *Eucalyptus*, chenopodium and ylang-ylang, oxazolidinones such as 4-decyloxazolidin-2-one, turpentine oil, pine oil, menthol.

According to the invention all of the aforementioned excipients and classes of excipients can be used without limitation alone or in any conceivable combination thereof, as long as the inventive use of a solubilisate is not thwarted, toxic actions may occur or the respective national legislations are infracted.

Thus the present application refers also to a cosmetic preparation according to the invention for cosmetic uses.

In a particularly preferred embodiment the present application refers also to a mouthwash comprising water and a solubilisate as defined in claim 6, wherein the at least one cosmetic agent is *Melaleuca ericifolia* essential oil and/or *Leptospermum petersonii* essential oil (see Example 9).

EXAMPLES

In the ensuing examples the relative quantities of the solubilizing agents can be changed inside the margins indicated for each component in the method according to the invention. The addition of glyceryl oleate and tocopherol is optional. An effective composition of the respective solubilizers was determined and filled up with MCT oil ad 100%.

It is possible to upscale or downscale the indicated amounts according to the desired absolute amount of the cosmetic agent to be solubilized in the solubilisate. The solubilisate can be portioned according to the desired final amount of the agent to be used by a customer.

Example 1: Solubilization of Salicylic Acid and Preparation of a Callus Removal Product Salicylic acid is often used in cosmetics because of its antimicrobial effects (up to 2 wt.-%). In higher concentrations it is used for the cosmetic treatment of acne, as it shows keratolytic and comedolytic actions, and for the cosmetic treatment of calluses, corns and warts.

Preparation of the Solubilisate

The following indications refer to the weight percent of the mixture. A solubilisate of ca. 10 ml was generated. Salicylic acid was provided, and then the solubilizing agents were admixed one by one under stirring for 5 min at room temperature (20±5° C.) and atmospheric pressure.

| | |
|---|---|
| salicylic acid | 10% |
| 1-palmitoyl-2-oleoyl-sn-glycero-3-phosphocholine (POPC) | 35% |
| MCT oil | 47.6% |
| mixture of 2-lysophosphatidylcholine and 2-lysophosphatidylcholine (1:1) | 2.6% |
| ethanol | 2.2% |
| oleic acid | 1.1% |
| glyceryl stearate | 1.2% |
| glyceryl oleate | 0.2% |
| beta-tocopherol | 0.1% |

Then the composition was cautiously heated under continued stirring, with an approximate temperature increment of 1° C./min. After ca. 35 min (ca. 55° C.) the composition started to become a clear solution. This solubilization process lasted for ca. 15 min more. Thus a solubilisate according to the invention was obtained after ca. 50 min at ca. 70° C. Then the heating and the stirring was stopped and the resulting solubilisate was allowed to cool down to room temperature. The solubilisate stayed clear and stable over an observation period of 4 months.

Preparation of a Callus Removal Product

The following ingredients are used (in weight-%):

| | |
|---|---|
| solubilisate of salicylic acid | 3.00% |
| cetyl alcohol (Lanette® 16) | 0.20% |
| glyceryl stearate, stearyl alcohol, sodium stearoyl lactylate, glyceryl stearate citrate (BLANOVA® MULS ECO 2277) | 5.00% |
| glyceryl stearate (Cutina® GMS) | 0.50% |
| octyldodecanol (Eutanol G) | 3.00% |
| dicaprylyl ether (Cetiol OE) | 3.50% |
| ethylhexyl palmitate (Cegesoft C 24) | 1.00% |
| pentanediol (1,4-pentanediol) | 5.00% |
| microcrystalline cellulose, algin (Avicel PC 815) | 1.00% |
| dehydroxanthan gum (AMAZE® XT) | 0.50% |
| glycerin (86%) | 5.00% |
| urea (urea pearls) | 25.00% |
| sodium hydroxide (50%) | q.s. |
| aqua | 47.30% |

In a first phase, 1,4-pentanediol, urea, glycerin, Avicel PC 815, AMAZE® XT and the needed amount of aqua and, if necessary, sodium hydroxide are mixed and heated to 70°-75° C. In a second phase, BLANOVA® MULS ECO 2277, Cutina® GMS, Lanette® 16, Eutanol G, Cetiol OE and Cegesoft C 24 are mixed and heated to 70°-75° C. Both phases are united at 70°-75° C. and homogenized. Then this mixture is allowed to cool down <35° C. Then said solubilisate of salicylic acid is added and homogenized.

Example 2: Solubilization of Coenzyme $Q_{10}$ and Preparation of a Skin Cream

Coenzyme $Q_{10}$ (synonyms: ubiquinone, ubidecarone, coenzyme Q, $CoQ_{10}$) is a ubiquitous coenzyme in most animals. Three redox states of coenzyme $Q_{10}$ have been described. The molecule acts as a two electron carrier and a one electron carrier, corresponding to its role in the electron transport chain and as a radical scavenger. Coenzyme $Q_{10}$ is hardly soluble in an aqueous environment and poorly absorbed in the body. It is also broadly marketed as an ingredient of cosmetic products, as it compensates for an age-related loss in coenzyme $Q_{10}$ in the skin. It has also antioxidant properties and is thus believed to be beneficial as an anti-aging agent.

Preparation of the Solubilisate

The following indications refer to the weight percent of the mixture. A solubilisate of ca. 10 ml was generated. Coenzyme $Q_{10}$ was provided, and then the solubilizing agents were admixed one by one under stirring for 5 min at room temperature (20±5° C.) and atmospheric pressure.

| | |
|---|---|
| coenzyme $Q_{10}$ | 4% |
| non-hydrogenated soy bean phosphatidylcholine | 26% |
| MCT oil | 62.95% |
| 2-lysophosphatidylcholine | 2.8% |
| ethanol | 1.8% |
| oleic acid | 0.9% |
| glyceryl stearate | 1.3% |
| glyceryl oleate | 0.2% |
| alpha-tocopherol | 0.05% |

Then the composition was cautiously heated under continued stirring, with an approximate temperature increment of 0.5° C./min. After ca. 36 min (ca. 38° C.) the composition started to become a clear solution. This solubilization process lasted for ca. 12 min more. Thus a solubilisate according to the invention was obtained after ca. 48 min at ca. 44° C. Then the heating and the stirring was stopped and the resulting solubilisate was allowed to cool down to room temperature. The solubilisate stayed clear and stable over an observation period of minimum 4 months.

Preparation of a Skin Cream

The following ingredients are used (in weight-%):

| | |
|---|---|
| solubilisate of coenzyme $Q_{10}$ | 3.00% |
| cetearyl alcohol (Lanette D®) | 6.60% |
| glyceryl stearate (Cutina MD®) | 4.15% |
| ceteareth 20 (Eumulgin B2®) | 0.40% |
| ceteareth 12 (Eumulgin B1®) | 1.25% |
| decyl oleate (Cetiol V®) | 2.50% |
| allantoin | 0.15% |
| perfume (scent Vanille doux) | 0.85% |
| sodium cetearyl sulfate (Lanette E®) | 0.65% |
| glycerin | 20.70% |
| phenoxyethanol, dehydroacetic acid, benzoic acid (Rokonsal ND®) | 1.00% |
| aqua | 58.75% |

In a first preparation, the solubilisate of coenzyme $Q_{10}$, cetearyl alcohol, glyceryl stearate, ceteareth 20, ceteareth 12, decyl oleate and sodium cetearyl sulfate were mixed and heated to 70° C. In a second preparation, allantoin, glycerin and aqua were mixed and heated to 70° C. Then the first preparation and the second preparation were slowly mixed and homogenized with a disperser (Ultra-Turrax T-18®) for 2 to 3 min. When cooled down to 35° C., a third preparation consisting of the perfume and Rokonsal ND® was added and homogeneously stirred. The mixture was rehomogenized at ca. 45° C. for 1 min. Then the resulting mixture was allowed to cool down to room temperature under stirring, herein avoiding the inclusion of air. If necessary, the pH can be adjusted with NaOH or citric acid.

The pH of the skin cream was 5.40. The stability of the skin cream was minimum 9 months at 40° C. At this temperature no phase separation occurred.

Example 3: Solubilization of *Boswellia sacra* Extract and Preparation of a Body Lotion

*Boswellia sacra* is the classic frankincense shrub. It is cultivated in Somalia, Yemen and Oman. Extracts from *Boswellia sacra* can be also used in cosmetic products. The main active agents of this extract are boswellic acids that comprise a number of pentacyclic triterpenes. They display anti-inflammatory actions by inhibiting the enzyme 5-lipooxygenase in a non-competitive manner. Thus the generation of leukotrienes is subdued. They have a skin-soothing effect. Allergic and/or inflammatory reactions of the skin can be mitigated by application of such an extract. The solubility in water of this extract is rather low.

Preparation of the Solubilisate

The following indications refer to the weight percent of the mixture. A solubilisate of ca. 10 ml was generated. *Boswellia sacra* extract was provided, and then a pre-prepared mixture of the solubilizing agents was admixed under stirring for 5 min at room temperature (20±5° C.) and atmospheric pressure.

| | |
|---|---|
| *Boswellia sacra* extract | 5% |
| mixture of dipalmitoyl phosphatidylcholine (DPPC) and dimyristoyl phosphatidylcholine (DMPC) (1:1) | 34% |
| MCT oil | 51.77% |
| 1-lysophosphatidylcholine | 3.2% |
| ethanol | 3.0% |
| oleic acid | 1.1% |
| glyceryl stearate | 1.7% |
| glyceryl oleate | 0.15% |
| ascorbyl palmitate | 0.08% |

Then the composition was cautiously heated under continued stirring, with an approximate temperature increment of 1.5° C./min. After ca. 39 min (ca. 79° C.) the composition started to become a clear solution. This solubilization process lasted for ca. 10 min more. Thus a solubilisate according to the invention was obtained after ca. 49 min at ca. 93° C. Then the heating and the stirring was stopped and the resulting solubilisate was allowed to cool down to room temperature. The solubilisate stayed clear and stable over an observation period of minimum 4 weeks.

Preparation of a Body Lotion

The following ingredients are used (in weight-%):

| | |
|---|---|
| solubilisate of *Boswellia sacra* extract | 1.00% |
| dicaprylyl carbonate (Cetiol CC ®) | 6.00% |
| caprylic/capric triglyceride (Myritol 312 ®) | 4.00% |
| polyglyceryl-3-diisostearate (Lameform TGI ®) | 2.00% |
| polyglyceryl-2-dipolyhydroxystearate (Dehymuls PGPH ®) | 2.00% |
| sodium chloride | 1.00% |
| zinc oxide/stearic acid (Sunjin SUNZnO-SA ®) | 1.00% |
| perfume (scent Sunny Emotion ®) | 2.00% |
| potassium sorbate | 0.65% |
| sodium benzoate | 0.60% |
| octyl dodecanol (Eutanol G ®) | 0.40% |
| *Cocos nucifera* seed butter | 3.00% |
| citric acid | 2.00% |
| aqua | ad 100% |

In a first preparation, the solubilisate of *Boswellia sacra* extract, dicaprylyl carbonate, caprylic/capric triglyceride, polyglyceryl-3-diisostearate, polyglyceryl-2-dipolyhydroxystearate, Sunjin SUNZnO-SA, octyl dodecanol and the *Cocos nucifera* seed butter are mixed and heated to 75° C. In a second preparation, sodium chloride, potassium sorbate, sodium benzoate and aqua are mixed and heated to 75° C. The pH of the second preparation is adjusted to 4.0 by means of citric acid. The first preparation and the second preparation are mixed and homogenized ((Ultra-Turrax T-18®) for 2 min at 75° C. Then the resulting mixture was allowed to cool down to 35° C. under stirring, herein avoiding the inclusion of air. Then the perfume was shortly homogenized and added. The final mixture was allowed to cool down to room temperature.

The viscosity of the resulting body lotion was 6172 mPa·s (Contraves Rheomat ER 108). When used in a 1:10 aqueous dilution the pH was 5.52. In a centrifuge test (3 min at 3,000 rpm), the body lotion showed to be stable. The stability of the body lotion was minimum 3 months at 40° C. At this temperature no phase separation occurred.

Example 4: Solubilization of Resveratrol and Preparation of a Hydrorganic Mask

Resveratrol (3,5,4'-trihydroxy-trans-stilbene) is an ingredient of a variety of plants such as grapes, raspberries, plums, peanuts, mulberries, blueberries, cranberries, bilberries, pines, cocoa bushes and Japanese knotweed. It acts as a phytoalexin to protect plants against injuries and bacterial or fungal infections. It is used as a dietary supplement, e.g. for promoting weight loss and as an anti-oxidative, and is associated with beneficial effects in vitro against tumors, neurodegenerative diseases such as Alzheimer's disease and glaucoma, cerebral blood flow disorders, heart diseases, type 2 diabetes and skin disorders. Due to a low bioavailability (absorption and a marked first-pass effect) the therapeutic use of resveratrol is limited until now. In cosmetics, it is used in anti-aging products and anti-wrinkle creams.

The solubility in water of this extract is rather low.

Preparation of the Solubilisate

The following indications refer to the weight percent of the mixture. A solubilisate of ca. 10 ml was generated. Resveratrol (Sabinsa, Germany) was provided, and then a pre-prepared mixture of the solubilizing agents was admixed under stirring for 5 min at room temperature (20±5° C.) and atmospheric pressure.

| | |
|---|---|
| resveratrol | 5% |
| natural egg phosphatidylcholine | 40% |
| MCT oil | 49.3% |
| L-alpha-lysophosphatidylcholine | 4% |
| ethanol | 1% |
| glyceryl stearate | 0.5% |
| glyceryl oleate | 0.2% |

Then the composition was cautiously heated in a closed vessel under continued stirring, with an approximate temperature increment of 1° C./min. After ca. 19 min (ca. 39° C.) the composition started to become a clear solution. This solubilization process lasted for ca. 7 min more. Thus a solubilisate according to the invention was obtained after ca. 26 min at ca. 46° C. Then the heating and the stirring was stopped and the resulting solubilisate was allowed to cool down to room temperature. The solubilisate stayed clear and stable over an observation period of 12 weeks.

Preparation of a Hydrorganic Mask

The following ingredients are used (in weight-%):

| | |
|---|---|
| solubilisate of resveratrol | 0.20% |
| hydroxypropyl starch phosphate (Structure XL National Starch) | 3.00% |
| sorbitan stearate (Span 60 Croda) | 3.00% |
| G sorbitan stearate, methyl glucose (Sympatens-O/2500) | 2.00% |
| isopropyl myristate | 3.00% |
| dicaprylyl carbonate (Cetiol CC Cognis) | 3.00% |
| dicaprylyl ether (Cetiol OE Cognis) | 1.00% |
| cetearyl alcohol (Nafol 1618 H Sasol) | 3.00% |
| cetyl palmitate (Sabowax CP Sabo) | 3.00% |
| aqua, hydrolyzed corn starch, beet root extract (DayMoist CLR) | 1.00% |
| ProBioBalance CLRTM Water, lactose, milk protein | 5.00% |
| phenoxyethanol, ethylhexyl glycerin (Euxyl PE 9010 ® Schülke) | 0.80% |
| perfume (Aqua Safe CS) | 0.30% |
| sodium hydroxide | 1.00% |
| aqua | ad 100% |

In a first phase, Structure XL National Starch, Span 60 Croda, Sympatens-O/2500 and the needed amount of aqua are mixed and heated to 70°-75° C. In a second phase, isopropyl myristate, Cetiol CC Cognis, Cetiol OE Cognis, Nafol 1618 H and Sabowax CP are mixed and heated to 70°-75° C. Both phases are united at 70°-75° C. and homogenized. Then this mixture is allowed to cool down <35° C. Then phase C consisting of said solubilisate of resveratrol, DayMoist CLR, ProBioBalance CLRTM Water, lactose, milk protein, Euxyl PE 9010 and Aqua Safe CS is added and homogenized. Finally, the pH is adjusted to 7.6 with sodium hydroxide.

Example 5: Comparison with Polysorbate 80 as the Major Solubilizing Agent

A similar experiment as in Example 4 was performed using polysorbate 80 as solubilizing agent instead of phosphatidylcholines with a lysophosphatidylcholine as co-solubilizer:

| | |
|---|---|
| resveratrol | 5.0% |
| polysorbate 80 | 44.0% |
| MCT oil | 49.3% |
| ethanol | 1.0% |
| glyceryl stearate | 0.5% |
| glyceryl oleate | 0.2% |

Then the composition was cautiously heated under continued stirring, with an approximate temperature increment of 1° C./min. After ca. 24 min (ca. 44° C.) the composition started to become a clear solution. This solubilization process lasted for ca. 8 min more. Thus a solubilisate according to the invention was obtained after ca. 32 min at ca. 52° C. Then the heating and the stirring was stopped and the resulting solubilisate was allowed to cool down to room temperature. In contrast to Example 4, resveratrol in the solubilisate started to precipitate upon cooling down. This result apparently did not depend on reasonable variations of the relative percentages of the respective excipients. Thus polysorbate 80 seems not to be suitable for substituting phosphatidylcholines with a lysophosphatidylcholine as co-solubilizer in such a solubilization process.

Example 6: Comparison with Polysorbate 80 as the Single Solubilizing Agent

A similar experiment as in Example 5 was performed using polysorbate 80 as the only solubilizing agent:

| | |
|---|---|
| resveratrol | 5% |
| polysorbate 80 | 95% |

Then the composition was cautiously heated under continued stirring, with an approximate temperature increment of 1° C./min. After ca. 26 min (ca. 46° C.) the composition started to become a clear solution. This solubilization process lasted for ca. 7 min more. Thus a solubilisate according to the invention was obtained after ca. 33 min at ca. 53° C. Then the heating and the stirring was stopped and the resulting solubilisate was allowed to cool down to room temperature. Similar to Example 5, resveratrol in the solubilisate started to become crystalline again upon cooling down. This shows that the failure of Example 5 apparently did not depend on the used auxiliary solubilizing agents.

Example 7: Solubilization of Sallow Thorn Oil and Preparation of a Massage Oil Sallow thorn (sea buckthorn; *Hippophae rhamnoides*) is a deciduous shrub reaching a height of 1-6 m and growing preferably on calcareous sand and gravelly soils in sunny places. An oil can be produced from its orange-colored berries that is rich in vitamins (vitamin C, E and K), carotenoids (such as beta-carotene, zeaxanthin and lycopene) and plant sterols (such as beta-sitosterol). Apart from its popular use against colds and febrile infections it is widely used in cosmetics in soaps, skin creams, hand creams, massage oils, shampoos etc. Soothing, caring, regenerative and moisturizing effects on the skin are known in the art.

Preparation of the Solubilisate

The following indications refer to the weight percent of the mixture. A solubilisate of ca. 10 ml was generated. Sallow thorn oil was provided, and then a pre-prepared mixture of the solubilizing agents was admixed under stirring for 5 min at room temperature (20±5° C.) and atmospheric pressure.

| | |
|---|---|
| sallow thorn oil | 15% |
| mixture of dimyristoyl phosphatidylcholine (DMPC) and 1-oleoyl-palmitoyl phosphatidylcholine (OPPC) (1:1) | 18% |
| MCT oil | 60.6% |
| 1-lysophosphatidylcholine | 2.2% |
| ethanol | 1.9% |
| myristic acid | 0.8% |
| glyceryl stearate | 1.2% |
| glyceryl oleate | 0.2% |
| ascorbyl palmitate | 0.1% |

Then the composition was cautiously heated under continued stirring, with an approximate temperature increment of 0.5° C./min. After ca. 42 min (ca. 41° C.) the composition started to become a clear solution. This solubilization process lasted for ca. 30 min more. Thus a solubilisate according to the invention was obtained after ca. 72 min at ca. 56° C. Then the heating and the stirring was stopped and the resulting solubilisate was allowed to cool down to room temperature. The solubilisate stayed clear and stable over an observation period of minimum 4 weeks.

Preparation of a Massage Oil

The following ingredients are used (in weight-%):

| | |
|---|---|
| solubilisate of sallow thorn oil | 2.0% |
| caprylic/capric triglyceride (Myritol 312 ®) | 27.0% |
| isopropyl myristate | 15.0% |
| caprylyl caprylate/caprate (Cetiol RLF ®) | 5.0% |
| passion flower oil (Cetiol PFO) | 2.0% |
| *Argania spinosa* oil (Argan oil) | 2.0% |
| perfume (GFP Orange/Lemongrass) | 0.5% |
| tocopherol (vitamin E) | 0.2% |
| *Helianthus Annuus* oil (sunflower oil) | ad 100% |

The solubilizing agents can be mixed in any order at room temperature and homogenized. Then the solubilisate of the sallow thorn oil is added and homogenized. Then the massage oil is ready for use.

Example 8: Solubilization of Lutein Esters and Preparation of a Sunscreen

Lutein esters are fatty acid esters of lutein, a xanthophyll (carotenoid) found in green leafy vegetables such as kale, spinach and carrots. The lutein molecule is able to absorb blue light and therefore appears yellow to orange, depending on the concentration. Therefore it has anti-oxidative properties and it can be used as a food dye. In cosmetics, lutein and lutein esters are marketed in antiaging products and as a UV radiation protector.

Preparation of the Solubilisate

The following indications refer to the weight percent of the mixture. A solubilisate of ca. 10 ml was generated. Lutein esters (DSM, Heerlen, The Netherlands) were provided, and then a pre-prepared mixture of the solubilizing agents was admixed under stirring for 5 min at room temperature (20±5° C.) and atmospheric pressure.

| | |
|---|---|
| lutein esters | 1% |
| non-hydrogenated soy bean phosphatidylcholine | 50% |
| MCT oil | 42.2% |
| 2-lysophosphatidylcholine | 3.65% |
| ethanol | 0.8% |
| oleic acid | 1.1% |
| glyceryl stearate | 1.0% |
| glyceryl oleate | 0.15% |
| delta-tocopherol | 0.1% |

Then the composition was cautiously heated under continued stirring, with an approximate temperature increment of 3° C./min. After ca. 18 min (ca. 75° C.) the composition started to become a clear solution. This solubilization process lasted for ca. 5 min more. Thus a solubilisate according to the invention was obtained after ca. 23 min at ca. 90° C. Then the heating and the stirring was stopped and the resulting solubilisate was allowed to cool down to room temperature. The solubilisate stayed clear and stable over an observation period of 3 weeks.

Preparation of a Sunscreen

The following ingredients are used (in weight %):

| | |
|---|---|
| solubilisate of lutein esters | 2.50% |
| titanium dioxide, dicaprylyl carbonate, polyglyceryl-3-diisostearate, stearic acid, aluminium hydroxide (Sun Jin GR-TD1 30.0) | 30.00% |
| silica, titanium dixoide (SUNSIL-Tin50) | 5.00% |
| dicaprylyl carbonate (Cetiol CC ®) | 8.00% |
| caprylic/capric triglyceride (Myritol 312 ®) | 5.00% |
| polyglyceryl-3-diisostearate (Lameform TGI ®) | 2.00% |
| polyglyceryl-2-dipolyhydroxystearate (Dehymuls PGPH ®) | 2.00% |
| sodium chloride | 1.00% |
| zinc oxide/stearic acid (Sunjin SUNZnO-SA ®) | 3.00% |
| perfume (Sunny day KVON ®) | 0.65% |
| potassium sorbate | 0.60% |
| sodium benzoate | 0.40% |
| aqua | ad 100% |

In a first phase, potassium sorbate, sodium benzoate, sodium chloride and the needed amount of aqua are mixed and heated to 70° to 75° C. In a second phase, Myritol 312, Cetiol CC, Lameform TGI, Dehymuls PGPH and Sun Jin GR-TD1 30.0 are mixed and heated to 70° to 75° C. Both phases are united at 70° to 75° C. and homogenized. Then this mixture is allowed to cool down <35° C. Then a third phase consisting of said solubilisate of lutein esters, SUN-SIL-Tin50, Sunjin SUNZnO-SA and Sunny day KVON is added and homogenized.

Example 9: Solubilization of Essential Oils for a Mouthwash

Most mouthwashes on the market contain ethanol in substantial amounts in order to get the rather active compounds solved therein. This is not popular with all consumers, and it is particularly inappropriate for children. Therefore there is a need for an alcohol-free mouthwash with anti-bacterial actions that could be swallowed by the consumer. Preferably, it should have a pleasant taste too.

*Melaleuca ericifolia* (swamp paperbark) is a tree from the myrtle family native to South-East Australia. The essential oil from *Melaleuca ericifolia* leaves contains a.o.1,8-cineole (eucalyptol) and α-pinene. Eucalyptol itself is insoluble in water. It provides a fresh mint-like smell and a spicy, cooling taste.

*Leptospermum petersonii* (lemon-scented teatree) is a shrub (up to 5 m) from the rain forests of the Australian east coast. The essential oil of the *Leptospermum petersonii* leaves provides a distinctive lemony aroma. Therefore it is used as a flavoring ingredient in tea blends. It has bactericidal and anti-mycotic properties (e.g. against *Candida albicans* and *Aspergillus fumigatus*).

Preparation of the Solubilisate

The following indications refer to the weight percent of the mixture. A solubilisate of ca. 10 ml was generated. Essential oils of *Melaleuca ericifolia* and *Leptospermum petersonii* were provided, and then a pre-prepared mixture of the solubilizing agents was admixed under stirring for 5 min at room temperature (20±5° C.) and atmospheric pressure.

| | |
|---|---|
| *Melaleuca ericifolia* essential oil | 3% |
| *Leptospermum petersonii* essential oil | 3% |
| 1-palmitoyl-2-oleoyl-sn-glycero-3-phosphocholine (POPC) | 25% |
| MCT oil | 62.65% |
| 1-lysophosphatidylcholine | 3.2% |
| propane-1-3-diol | 0.8% |
| oleic acid | 1.1% |
| glyceryl stearate | 1.0% |
| glyceryl oleate | 0.15% |
| gamma-tocopherol | 0.1% |

Then the composition was cautiously heated under continued stirring, with an approximate temperature increment of 0.5° C./min. After ca. 30 min (ca. 35° C.) the composition started to become a clear solution. This solubilization process lasted for ca. 6 min more. Thus a solubilisate according to the invention was obtained after ca. 35 min at ca. 38° C. Then the heating and the stirring was stopped and the resulting solubilisate was allowed to cool down to room temperature. The solubilisate stayed clear and stable over an observation period of 6 months.

Several drops of this solubilisate can be added from a standard dispenser. to a glass of tap water, alternatively mineral water. This mouthwash is ready for use.

The invention claimed is:

1. A method for solubilizing poorly water-soluble organic cosmetic agents, comprising the following steps:

a) providing at least one poorly water-soluble organic cosmetic agent having in total a range of 0.5% to 25% per weight at room temperature and a pressure of 0.2 bar to 1 bar;
b) adding, in any sequence, solubilization agents, comprising:
   at least one phosphatidylcholine having in total a range of 20% to 80% per weight,
   wherein the at least one phosphatidylcholine is non-hydrogenated soybean PC, DMPC, POPC or DOPC,
   at least one medium-chained triglyceride having in total a range of 10% to 70% per weight,
   at least one lysophosphatidylcholine having in total a range of 1% to 15% per weight,
   wherein the ratio of phosphatidylcholines to lysophosphatidylcholines is in the range of 80:1 per weight to 1.33:1 per weight,
   ethanol in the range of 1% to 20% per weight, and oleic acid in the range of 0.5% to 10% per weight, respectively,
   wherein relative weight percentages add up to 100% and all solubilization agents are independently from one another cosmetically acceptable excipients;
c) heating the resulting mixture by continuously increasing the temperature with a temperature increment of 0.5° C./min to 3° C./min over a period of 15 to 60
d) stopping the temperature increase in a temperature range of 30° C. to 125° C. as soon as a clear solution is reached; and
e) letting the resulting solubilisate cool down to room temperature.

2. The method according to claim 1, wherein additionally in step b) at least one antioxidant in the overall range of 0.01 to 10% per weight is added, said at least one antioxidant being a cosmetically acceptable excipient.

3. The method according to claim 2, wherein said at least one antioxidant is ascorbyl palmitate.

4. A solubilisate of at least one poorly water-soluble organic cosmetic agent, produced by a method as defined in claim 1.

5. A cosmetic preparation comprising a hydrophilic cosmetic base and the solubilisate according to claim 4.

6. A cosmetic preparation comprising a lipophilic cosmetic base and the solubilisate according to claim 4.

7. The solubilisate according to claim 4, wherein the solubilisate masks an unpleasant odor of the at least one poorly water-soluble organic cosmetic agent.

8. The solubilisate according to claim 4, in which the solubilisate of the at least one poorly water-soluble organic cosmetic agent enhances the skin penetration of at least one of said cosmetic agents.

9. The solubilisate according to claim 4, in which the at least one poorly water-soluble organic cosmetic agent is selected from the group containing salicylic acid, coenzyme $Q_{10}$, *Boswellia sacra* extract, resveratrol, sallow thorn oil, lutein esters, *Melaleuca ericifolia* essential oil and *Leptospermum petersonii* essential oil.

10. A cosmetic preparation comprising the solubilisate as defined in claim 4 and at least one cosmetically acceptable excipient.

11. The cosmetic preparation according to claim 10, wherein the at least one cosmetic excipient is selected from the group comprising acidifiers, alkalization agents, neutralization agents, antioxidants, binding agents, colorants, pigments, nanopigments, moisturizers, humectants, resins, preservatives, oxidizing agents, reducing agents, stabilizers, opacifiers, pearl shine pigments, denaturants, plasticizers, fragrances, surfactants, diluents, fillers and solubilizers.

12. The cosmetic preparation according to claim 11, further comprising at least one penetration enhancer.

13. A mouthwash comprising water and a solubilisate as defined in claim 4, wherein the at least one poorly water-soluble organic cosmetic agent is *Melaleuca ericifolia* essential oil and/or *Leptospermum petersonii* essential oil.

* * * * *